United States Patent
Orr et al.

(10) Patent No.: US 8,800,561 B2
(45) Date of Patent: Aug. 12, 2014

(54) SYSTEM, METHOD AND APPARATUS FOR REMOVAL OF VOLATILE ANESTHETICS FOR MALIGNANT HYPERTHERMIA

(76) Inventors: Joseph Orr, Park City, UT (US); Dwayne Westenskow, Salt Lake City, UT (US); Derek Sakata, Salt Lake City, UT (US)

( * ) Notice: Subject to any disclaimer, the term of this patent is extended or adjusted under 35 U.S.C. 154(b) by 5 days.

(21) Appl. No.: 13/600,952

(22) Filed: Aug. 31, 2012

(65) Prior Publication Data

US 2012/0325213 A1 Dec. 27, 2012

Related U.S. Application Data

(62) Division of application No. 12/431,644, filed on Apr. 28, 2009.

(51) Int. Cl.
| | | |
|---|---|---|
| *A62B 7/10* | (2006.01) | |
| *A62B 19/00* | (2006.01) | |
| *A62B 23/02* | (2006.01) | |
| *A61M 16/00* | (2006.01) | |

(52) U.S. Cl.
CPC .......... *A61M 16/009* (2013.01); *A61M 16/0093* (2013.01)
USPC .................................................. 128/205.12

(58) Field of Classification Search
CPC .......... A61M 16/009; A61M 16/0093; A61M 16/105; A61M 16/107; A61M 16/106; A61M 16/1065
USPC ............. 128/205.12, 205.27–205.29, 201.13, 128/204.16, 200.24, 910
See application file for complete search history.

(56) References Cited

U.S. PATENT DOCUMENTS

| | | | | |
|---|---|---|---|---|
| 404,986 | A | * | 6/1889 | Rudolfy .................... 128/202.13 |
| 3,566,867 | A | * | 3/1971 | Dryden .................... 128/205.28 |
| 4,195,627 | A | * | 4/1980 | Haertle .................... 128/202.26 |
| 4,318,398 | A | * | 3/1982 | Oetjen et al. ............ 128/201.13 |
| 4,334,533 | A | * | 6/1982 | Henkin .................... 128/205.28 |
| 4,360,018 | A | | 11/1982 | Choksi |
| 5,036,842 | A | | 8/1991 | van der Smissen et al. |
| 5,044,361 | A | * | 9/1991 | Werner et al. ........... 128/204.16 |
| 5,195,527 | A | * | 3/1993 | Hicks ....................... 128/205.12 |
| 5,482,031 | A | * | 1/1996 | Lambert .................. 128/203.12 |

(Continued)

OTHER PUBLICATIONS

Gunter et al., *Preparation of the Dräger Fabius Anesthesia Machine for the Malignant-Hyperthermia Susceptible Patient*, International Anesthesia Research Society, vol. 107, No. 6, Dec. 2008.

*Primary Examiner* — Tan-Uyen T Ho
*Assistant Examiner* — Bradley Philips
(74) *Attorney, Agent, or Firm* — Bateman IP

(57) ABSTRACT

Systems, methods, and apparatus for removing volatile anesthetics from an anesthesia or ventilation system to minimize the effects of malignant hyperthermia in susceptible patients. According to one aspect of the present invention, a system for removing volatile anesthetics is provided. A first filter component placed in fluid communication with an inspiratory limb of an anesthesia or ventilation system such that volatile anesthetics will pass through the first filter component during operation of the anesthesia or ventilation system. A second filter component is operably coupled to the expiration port of the anesthesia or ventilation system such that gases passing through the expiratory limb of the anesthesia or ventilation system pass through the second filter component. The first filter component and second filter component are adapted to effectively remove volatile anesthetics passing through the respective filters.

19 Claims, 15 Drawing Sheets

(56) References Cited

U.S. PATENT DOCUMENTS

| | | | |
|---|---|---|---|
| 5,771,885 A * | 6/1998 | Putrello | 128/205.27 |
| 5,983,894 A * | 11/1999 | Fukunaga et al. | 128/205.29 |
| 6,095,135 A * | 8/2000 | Clawson et al. | 128/201.13 |
| 6,467,481 B1 * | 10/2002 | Eswarappa | 128/206.17 |
| 6,523,538 B1 * | 2/2003 | Wikefeldt | 128/204.18 |
| 6,550,476 B1 * | 4/2003 | Ryder | 128/201.13 |
| 6,634,355 B2 | 10/2003 | Colas | |
| 6,733,556 B1 * | 5/2004 | Luigi | 55/385.1 |
| 6,805,118 B2 | 10/2004 | Brooker et al. | |
| 7,077,134 B2 * | 7/2006 | Ahlmen | 128/205.12 |
| 7,077,136 B2 * | 7/2006 | Ahlmen et al. | 128/205.27 |
| 7,634,998 B1 * | 12/2009 | Fenley | 128/201.13 |
| 7,921,846 B1 * | 4/2011 | Marler et al. | 128/205.24 |
| 7,926,484 B2 * | 4/2011 | Dhuper et al. | 128/203.15 |
| 8,240,308 B2 * | 8/2012 | Clemensen et al. | 128/205.28 |
| 8,267,081 B2 * | 9/2012 | Flanagan et al. | 128/203.16 |
| 8,267,087 B2 * | 9/2012 | Wruck et al. | 128/205.27 |
| 8,286,630 B2 * | 10/2012 | Ogasahara | 128/201.13 |
| 2001/0029949 A1 * | 10/2001 | Blackhurst et al. | 128/205.12 |
| 2001/0047804 A1 * | 12/2001 | Fukunaga et al. | 128/205.27 |
| 2002/0017302 A1 * | 2/2002 | Fukunaga et al. | 128/207.14 |
| 2004/0118402 A1 * | 6/2004 | Heinonen | 128/204.18 |
| 2004/0149281 A1 * | 8/2004 | Ahlmen | 128/203.12 |
| 2006/0219243 A1 * | 10/2006 | Walstrom | 128/201.13 |
| 2007/0068518 A1 * | 3/2007 | Urias et al. | 128/200.24 |
| 2007/0157929 A1 * | 7/2007 | Radomski et al. | 128/204.18 |
| 2007/0215159 A1 * | 9/2007 | Ross et al. | 128/205.28 |
| 2008/0041385 A1 * | 2/2008 | Orr et al. | 128/205.12 |
| 2009/0095296 A1 | 4/2009 | Wruck et al. | |
| 2009/0301477 A1 * | 12/2009 | Pierro et al. | 128/201.13 |
| 2009/0301479 A1 * | 12/2009 | Pedarzini et al. | 128/201.13 |
| 2010/0126509 A1 * | 5/2010 | Chang | 128/205.12 |
| 2012/0192863 A1 * | 8/2012 | Power et al. | 128/201.13 |
| 2012/0227741 A1 * | 9/2012 | Cegla | 128/205.12 |
| 2012/0266881 A1 * | 10/2012 | Borm et al. | 128/204.16 |

\* cited by examiner

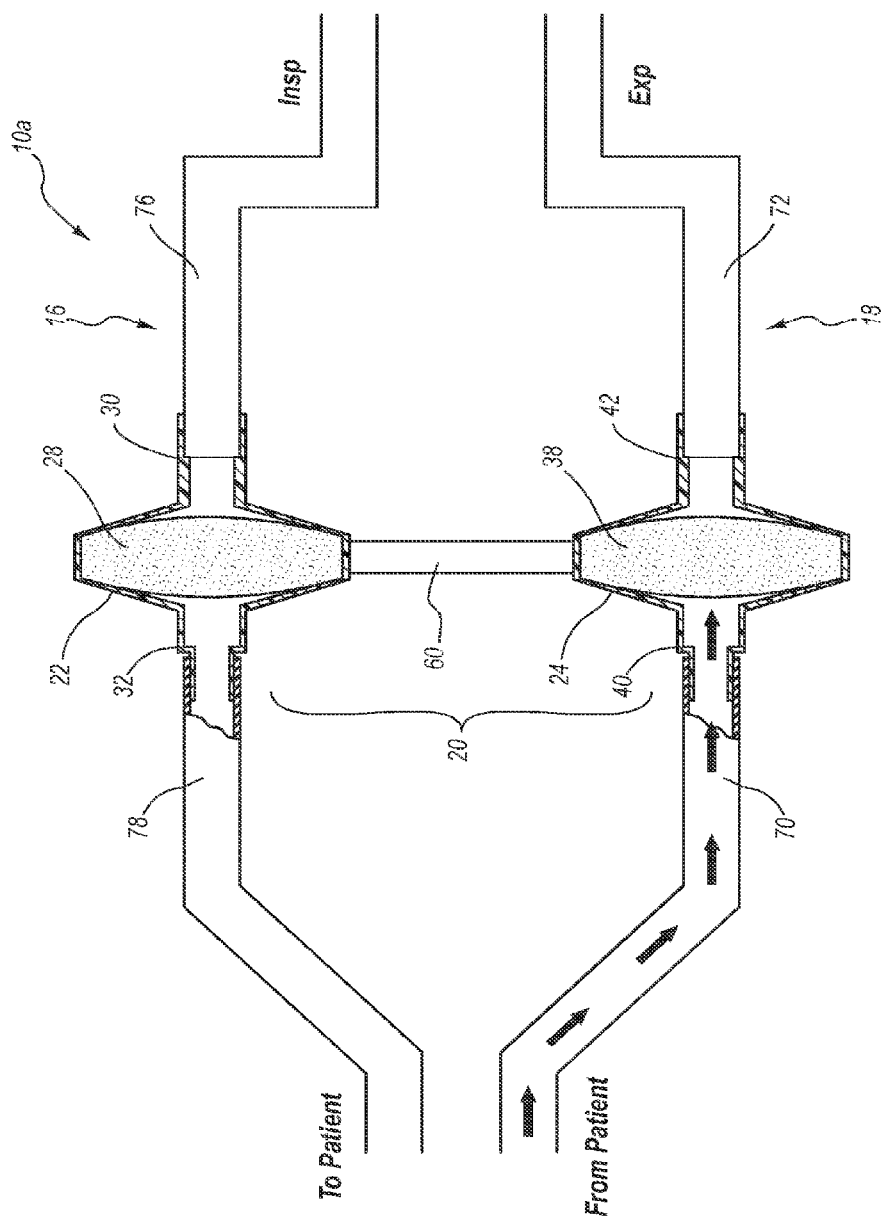

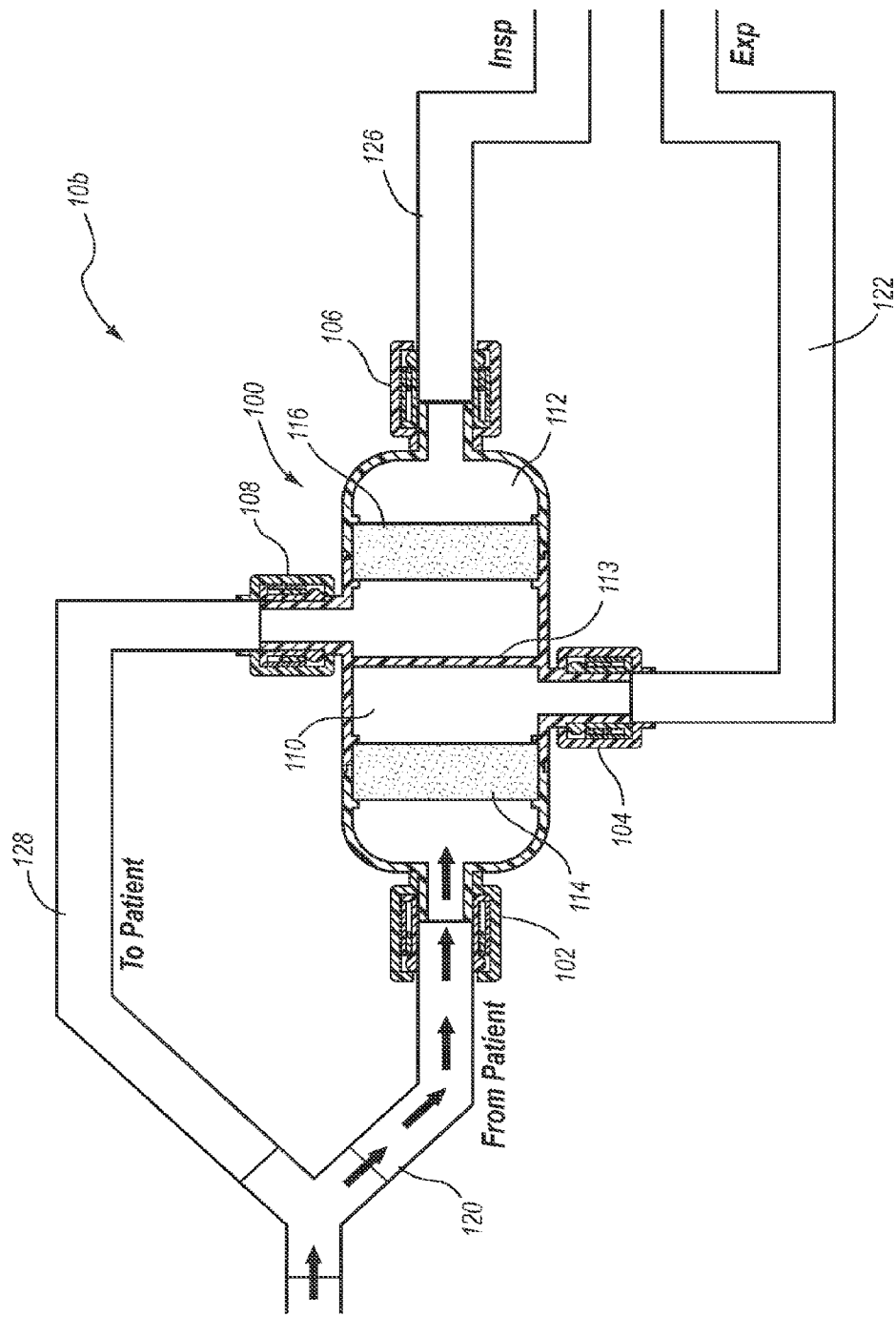

SYSTEM, METHOD AND APPARATUS FOR REMOVAL OF VOLATILE ANESTHETICS FOR MALIGNANT HYPERTHERMIA

The present application is a divisional application of U.S. patent application Ser. No. 12/431,644, filed Apr. 28, 2009, which is incorporated herein by reference in its entirety.

BACKGROUND OF THE INVENTION

1. Field of the Invention

The present invention relates to systems, methods and apparatus for the removal of volatile anesthetics from an anesthesia or ventilation system. In more particular, the present invention relates to a two-part or dual filter apparatus for removal of volatile anesthetics, the filter apparatus being adapted to be utilized with an anesthetic or ventilation system to facilitate the removal of inhaled or volatile anesthetics from the system intra-operatively or before the beginning of an anesthetic procedure to prevent or remedy a malignant hyperthermic response within a patient.

2. Relevant Technology

Malignant hyperthermia is a biochemical chain reaction response which can be triggered by commonly utilized inhaled anesthetics and the paralyzing agent succinylcholine within the skeletal muscles of susceptible individuals. The general signs of a malignant hyperthermia crisis include tachycardia, a greatly increased body metabolism, muscle rigidity and/or fever that may exceed 110 degrees Fahrenheit. Severe complications of malignant hyperthermia include, cardiac arrest, brain damage, internal bleeding or failure of other body systems. As a result, a secondary cardiovascular collapse resulting in the patient's death can occur if the patient's malignant hyperthermic reaction is not quickly identified and remedied by the practitioner.

Malignant hyperthermia susceptible persons have a mutation that results in the presence of abnormal proteins in the muscle cells of their body. Although normal in everyday life, when these patients are exposed to certain inhaled volatile anesthetic agents, it causes an abnormal release of calcium inside the muscle cell, which results in a sustained muscle contraction and the abnormal increase in energy utilization and heat production. The muscle cells eventually run out of energy, and die releasing large amounts of potassium into the bloodstream, which can lead to heart rhythm abnormalities. The muscle pigment myoglobin is also released which may be toxic to the patient's kidneys. Left untreated, these changes can cause cardiac arrest, kidney failure, blood coagulation problems, internal hemorrhage, brain injury, liver failure, and may be fatal.

The exact incidence of malignant hyperthermia is unknown. Some of the current medical literature estimates the rate of occurrence to be as frequent as one in 5,000 or as rare as one in 65,000 administrations of general anesthesia with triggering agents. The incidence varies depending on the concentration of malignant hyperthermia susceptible families in a given geographic area.

When a patient unexpectedly experiences a malignant hyperthermia reaction, after the patient is anesthetized and the surgery has begun, different protocols are utilized to treat the patient. In this case, it is necessary to turn off the anesthetic vaporizer, increase the fresh gas flow to flush the vapor for the breathing circuit and increase patient ventilation. The actions of turning off the anesthesia vaporizer and increasing fresh gas flow decrease the amount of vapor that is re-circulated to the patient, but they do not eliminate it. During the first minutes after the anesthesia vaporizer has been turned off, the patient continues to exhale a significant volume of anesthetic vapor. Due to the closed loop configuration of many anesthesia delivery machines, some of this previously exhaled vapor is inevitably re-inhaled.

The other situation in which malignant hyperthermia will be addressed by a practitioner is in the preparation of an anesthesia machine for use in a patient that is known, or suspected, to be susceptible to malignant hyperthermia. In this situation, the exigencies of the medical procedure can necessitate the use all of the capabilities of the anesthesia machine including ventilation, monitoring, oxygen delivery, etc. with the notable exception that delivery of volatile anesthetic vapor will not be utilized. When an anesthesia machine is to be utilized with a patient that is susceptible to malignant hyperthermia, residual anesthetic vapor must be thoroughly scrubbed from the machine until the residual vapor concentration in the gas delivered by the machine to the patient is below the suggested limit of 5 parts per million. Because some of the parts in newer anesthesia machines are made of plastic materials that tend to retain anesthetic gases, clearing the anesthetic gases completely from the machine can take hours. In fact, many hospitals have protocols that require the machine to be flushed for multiple hours before use in these patients, or require that a "clean" machine that has been in storage be used in malignant hyperthermia susceptible patents. As will be appreciated, not only is the use of such protocols time consuming, but the anesthesia machine is unable to be utilized in other anesthesia procedures during this time, resulting in increased costs and inefficiency in use of the hospitals capital equipment.

It has been shown that placing a charcoal filter on the inspired limb of the anesthesia machine effectively removes the residual anesthetic so that the machine can be used immediately. However, there is a risk that the filter be placed incorrectly on the expired limb of the anesthesia circuit. Additionally, the use of a single thick filter needed to adsorb inhaled anesthetics can result in undesirable increase in back pressure limiting the ease of gas delivery to the patient. Finally, placement of a single filter on the inspired limb does not address the reintroduction of inhaled anesthetics back to the system from patients who have already been administered such anesthetics. Furthermore, using only a single filter does not preclude the accidental placement of the filter on the incorrect limb of the anesthesia or ventilator system.

BRIEF DESCRIPTION OF THE DRAWINGS

FIGS. 3A-3D are schematic views of a dual filter assembly illustrating operation of a dual filter assembly with an expiratory and inspiratory limb of an anesthesia or ventilation system according to one aspect of the present invention.

FIGS. 6A-6D illustrate the use of a two-part filter apparatus with an inspiratory limb and an expiratory limb of an anesthesia or ventilation system according to one aspect of the present invention.

BRIEF SUMMARY OF THE INVENTION

Figure 1:
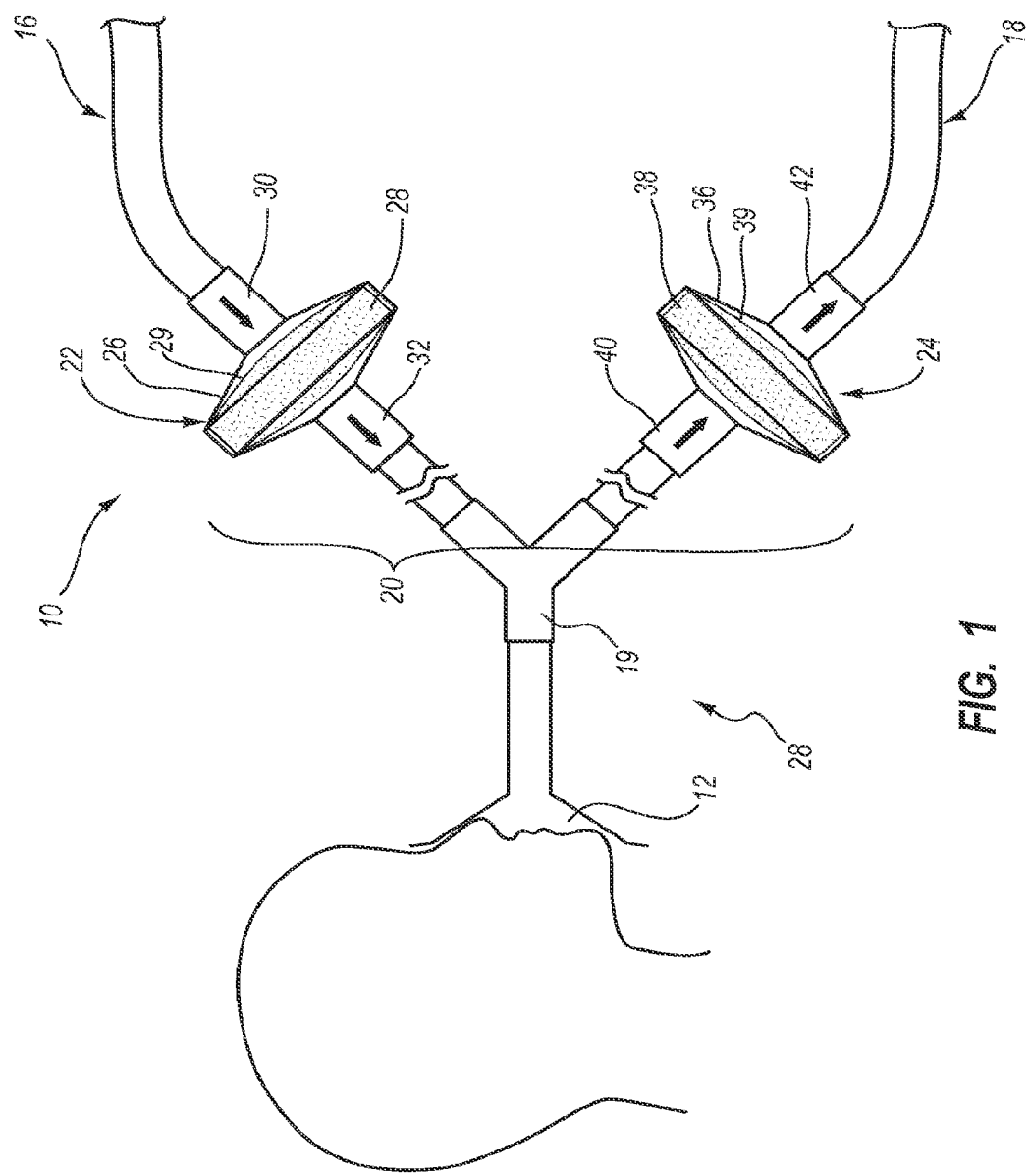
FIG. 1 is a schematic view of a system and apparatus for the removal of anesthesia from an anesthesia or ventilation system according to one aspect of the present invention.

The present invention relates to systems, methods, and apparatus for removing volatile anesthetics from an anesthesia or ventilation system to minimize the effects of malignant hyperthermia in susceptible patients. According to one aspect of the present invention, a system for removing volatile anesthetics is provided. In the embodiment, a first filter component is placed in fluid communication with an inspiratory limb of an anesthesia or ventilation system such that volatile anesthetics will pass through the first filter component during operation of the anesthesia or ventilation system. A second filter component is operably coupled to the expiration port of the anesthesia or ventilation system such that gases passing through the expiratory limb of the anesthesia or ventilation system pass through the second filter component. The first filter component and second filter component are adapted to adsorb and effectively remove volatile anesthetics passing through the respective filters.

The use of the first and second filter component results in removal of volatile anesthetics flowing through the anesthesia or ventilation system. In more particular, the configuration of the filter apparatus allows removal of volatile anesthetics from both the inspiratory and expiratory limbs of the anesthesia or ventilation system. In the intra-operative application, not only is the rate of removal of volatile anesthetic from the system increased, but a patient is only required to breathe through one of the filters. As a result, overall resistance to breathing experienced by the patient is substantially decreased. In other words, as a user exhales, the amount of exhaled breath from the patient is required to pass through only a single filter. As the patient inhales, the patient's breath similarly only passes through a single filter. As a result, resistance to breathing experienced by the patient and the requirements to overcome the resistance provided by the filter are substantially decreased. Additionally, the rate of removal of anesthetic is increased over that which would be provided by the use of a single filter.

According to one aspect of the present invention, an apparatus for removing volatile anesthetics from a patient is provided. According to one illustrative aspect of the present invention, the apparatus for removing volatile anesthetics from an anesthesia or ventilation system comprises a first filter component and a second filter component operatively connected to the first filter component. In the embodiment, the first filter component is operatively connected to the inspiration limb of the anesthesia or ventilation system. Additionally, a second filter component is operatively coupled to the expiration limb of the anesthesia or ventilation system. By providing a dual filter assembly in connection with the apparatus for removing volatile anesthetics from the ventilation system, volatile anesthetics can be removed from the system, both during inspiration and expiration during the course of a procedure.

According to yet another aspect of the present invention, the dual filter assembly comprises a first filter and a second filter which are connected by a strap, arm, housing component or other member such that both the first filter component and the second filter component are readily accessible when removal of the volatile anesthetic is required in connection with an anesthesia or ventilation system. According to another embodiment of the present invention, the apparatus for removing volatile anesthetics comprises a two-part filter apparatus in which both a first filter component and second filter component are provided within a single housing. According to one aspect of the present invention, the inlet ports of the filter components comprise a female connector and the outlet components comprise a male connector such that accidental or inadvertent mistakes in connecting the filter apparatus to the anesthesia or ventilation system are minimized. In another embodiment, filters are attached to the inspiratory and expiratory hoses of the breathing circuit such that when the breathing circuit is replaced, the charcoal filters are correctly installed on the anesthesia machine.

Additional aspects and advantages will be apparent from the following detailed description of preferred embodiments, which proceeds with reference to the accompanying drawings.

DETAILED DESCRIPTION

The present invention relates to systems, methods, and apparatus for removing volatile anesthetics from an anesthesia or ventilation system to minimize the effects of malignant hyperthermia in susceptible patients. According to one aspect of the present invention, a system for removing volatile anesthetics is provided. In the embodiment, a first filter component is placed in fluid communication with an inspiratory limb of an anesthesia or ventilation system such that volatile anesthetics will pass through the first filter component during operation of the anesthesia or ventilation system. A second filter component is operably coupled to the expiration port of the anesthesia or ventilation system such that gases passing through the expiratory limb of the anesthesia or ventilation system pass through the second filter component. The first filter component and second filter component are adapted to adsorb and effectively remove volatile anesthetics passing through the respective filters. As will be appreciated by those skilled in the art, inspiratory and expiratory limbs of the system typically will comprise hoses of the breathing circuit, but may be representative of any portion of the system within the inspiratory and expiratory pathway including portions of the system within the anesthesia machine. As such, discussion of the inspiratory and expiratory limbs should not be considered to be limiting in nature, but is provided for the sake of clarity and to provide an explanation of the manner in which a filter assembly or dual filter apparatus can be utilized within the system.

The use of the first and second filter component result in removal of volatile anesthetics flowing from the anesthesia or ventilation system to the patient. In more particular, the configuration of the filter apparatus allow removal of volatile anesthetics from both the inspiratory and expiratory limbs of the anesthesia or ventilation system. In the intra-operative application, not only is the rate of removal of volatile anesthetic from the circle breathing system increased, but a patient is only required to breathe through one of the filters during each phase of respiration. As a result, overall resistance to breathing experienced by the patient is substantially decreased. In other words, as a user exhales, the amount of exhaled breath from the patient is required to pass through only a single filter. As the patient inhales, the patient's breath similarly only passes through a single filter. As a result, resistance to breathing experienced by the patient and the requirements to overcome the resistance provided by the filter are substantially decreased. The rate of removal of anesthetic is increased over that which would be provided by the use of a single filter. Additionally, the patient is protected from inhaling potentially toxic anesthetic vapors even if the one-way valves in the anesthesia machine fail.

FIG. 1 is a component view of an anesthesia/ventilation system 10 according to one aspect of the present invention. In the illustrated embodiment, anesthesia/ventilation system 10 is utilized to provide an amount of gas to a patient or to otherwise facilitate ventilation of a patient. Anesthesia/ventilation system 10 can be utilized to introduce anesthesia to a patient during the course of a procedure. Anesthetics utilized with anesthesia/ventilation system 10 will typically include volatile anesthetic which can be inhaled by the patient during the course of an operation. Additionally, anesthesia/ventilation system 10 can be utilized to facilitate patient ventilation to maintain desired patient respiration in response to the effects of volatile anesthetics or when the patient is otherwise experiencing difficulty breathing.

In the illustrated embodiment, anesthesia/ventilation system 10 comprises a mask 12, an inspiratory limb 16, and an expiratory limb 18. Mask 12 is adapted to be positioned over the nose and mouth of the patient to facilitate the delivery of gases to be delivered to the patient. As will be appreciated by those skilled in the art, mask 12 is provided for illustrative purposes. Anesthesia/ventilation system 10 can include other patient delivery mechanisms such as an endotracheal tube, laryngeal mask airway or other respiratory patient interface mechanism.

Inspiratory limb 16 is operatively connected to mask 12 such that as the patient inhales, gases are delivered to the patient. In the absence of filters 24 and 28, such gases are configured to provide desired properties or compositions, such as air, oxygen, and/or inhaled anesthetics. Expiratory limb 18 is also positioned in fluid communication with mask 12. Expiratory limb 18 allows gases that are being exhaled from the patient to be transmitted away from the patient. Once the gases are transmitted from the patient, they can then either be expelled to the external environment, or returned to the anesthesia/ventilation system 10 for recirculation.

In the illustrated embodiment, a dual filter assembly 20 is illustrated. Dual filter assembly 20 comprises an anesthesia removal apparatus in the illustrated embodiment. Dual filter assembly 20 comprises a first filter component 22 and a second filter component 24. First filter component 22 is operatively coupled to inspiratory limb 16. Second filter component 24 is operatively coupled to expiratory limb 18. By connecting first filter component 22 to inspiratory limb 16 and second filter component 24 to expiratory limb 18, any volatile anesthetics that are circulating within the anesthesia/ventilation system 10 are absorbed and effectively removed from the gases that the patient breaths. In this manner, in the event that a patient experiences malignant hyperthermia symptoms, a practitioner can quickly and easily actuate/install dual filter assembly 20 in connection with anesthesia/ventilation system 10. If a patient has a known or suspected susceptibility to malignant hyperthermia, the practitioner can install dual filter assembly 20 prior to use of the anesthesia/ventilation system 10 for the patient, minimizing the potential that toxic residual amounts of volatile anesthetic gas will reach the patient.

In the illustrated embodiment, first filter component 22 comprises a housing 26, a filter 28, a filter cavity 29, an inlet port 30 and an outlet port 32. Housing 26 comprises an external framework for supporting the other components of first filter component 22. Housing 26 forms a filter cavity 29 on the interior of first filter component 22. Filter cavity 29 is adapted to accommodate a filter 28. Filter 28 can comprise any of a variety of known filter mechanisms which can be utilized to remove volatile anesthetics from a patient in a desired manner. Filter 28 is provided in fluid communication with inlet port 30 and outlet port 32. Inlet port 30 is positioned on the distal portion of housing 26. In one embodiment, inlet port 30 is adapted to be coupled with tubing associated with inspiratory limb 16. In another embodiment, inlet port 30 is adapted to be coupled directly to a nipple of an anesthesia delivery device.

Outlet port 32 is positioned on the proximal portion of housing 26. Outlet port 32 is adapted to be connected to tubing associated with inspiratory limb 16 on the portion of the inspiratory limb 16 positioned proximal to the patient. According to one embodiment of the present invention, the configuration of inlet port 30 and outlet port 32 have different shapes or configurations to facilitate the desired assembly of first filter component 22 with the inspiratory limb 16 and/or components of the anesthesia/ventilation system 10. For example, in one embodiment of the present invention, one of inlet port 30 and outlet port 32 comprises a male connector. The other of inlet port 30 and outlet port 32 comprises a female connector. In this manner, the practitioner can quickly and simply ascertain which of the inlet and outlet ports to connect to the distal portion of the inspiratory limb and which of the inlet port 30 and outlet port 32 to connect to the proximal portion of the inspiratory limb 16. In this manner, correct coupling and operation of first filter component 22 can be maintained even where a practitioner is focused on other aspects of a procedure to be performed.

In the illustrated embodiment, a second filtering component 24 is illustrated. Second filter component 24 comprises a housing 36, a filter 38, a filter cavity 39, an inlet port 40 and an outlet port 42. Housing 36 comprises an external framework for supporting the other components of second filter component 24. Housing 36 forms a filter cavity 39 on the interior of second filter component 24. Filter cavity 39 is adapted to accommodate filter 38. Filter 38 can comprise any of a variety of known filter mechanisms which can be utilized to remove volatile anesthetics from a patient in a desired manner. Filter 38 is provided in fluid communication with inlet port 40 and outlet port 42. Inlet port 40 is positioned on the distal portion of housing 36. Inlet port 40 is adapted to be coupled with tubing associated with inspiratory limb 16.

Outlet port 42 is positioned on the distal portion of housing 36. In one embodiment, outlet port 32 is adapted to be connected to tubing associated with expiratory limb 18 on the portion of the expiratory limb 18 positioned distal to the patient. In another embodiment, inlet port 40 is adapted to be coupled directly to a nipple of an anesthesia delivery device. According to one embodiment of the present invention, the configuration of inlet port 40 and outlet port 42 have different shapes or configurations to facilitate the desired assembly of second filter component 24 with the expiratory limb 18. For example, in one embodiment of the present invention, one of inlet port 40 and outlet port 42 comprises a male connector. The other of inlet port 40 and outlet port 42 comprises a female connector. In this manner, the practitioner can quickly and simply ascertain which of the inlet and outlet ports to connect to the distal portion of the expiratory limb 18 or other component of anesthesia delivery device and which of the inlet port 40 and outlet port 42 to connect to the proximal portion of the expiratory limb 18. In this manner, correct coupling and operation of second filter component 24 can be maintained even where a practitioner is focused on other aspects of a procedure to be performed.

As will be appreciated by those skilled in the art, a variety of types and configurations of systems and apparatus for removing volatile anesthetics from an anesthesia or ventilation system can be utilized without departing from the scope and spirit of the present invention. For example, according to one embodiment of the present invention, the anesthesia/ventilation system comprises any mechanism which facilitates the ventilation of the patient. According to another embodiment of the present invention, the particular components which are utilized in connection with the ventilation system can vary in terms of being added to or subtracted from without departing from the scope and spirit of the present invention. According to yet another embodiment of the present invention, the first filter and second filter components comprise a charcoal filter. According to another embodiment of the present invention, the first filter component and the second filter component comprise other known filtering apparatus. According to yet another embodiment of the present invention, the first filter component and second filter component are placed on other components of the anesthesia/ventilation system other than the inspiratory and expiratory limb.

Figure 2:
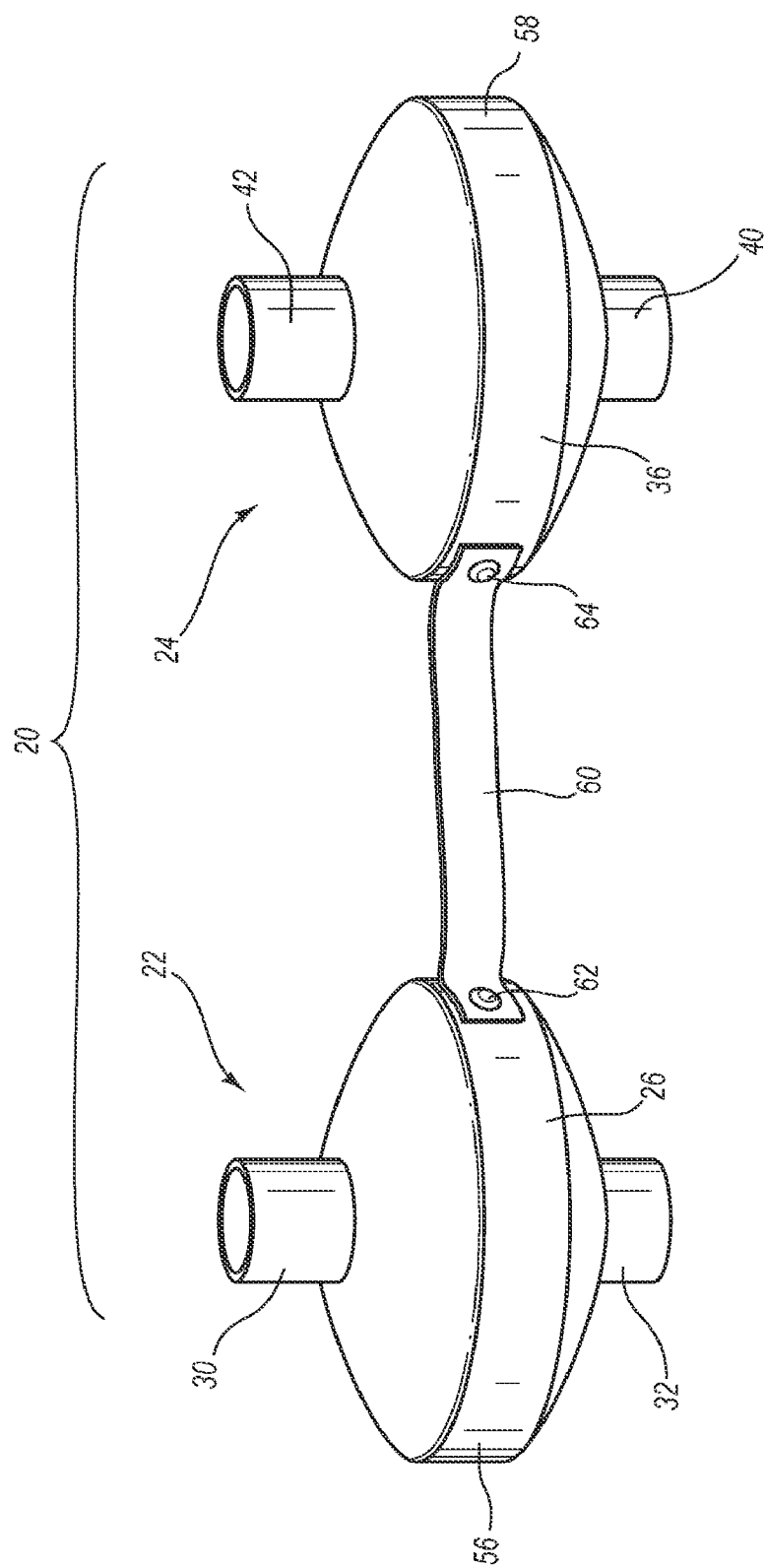
FIG. 2 is a perspective view of a dual filter assembly for use with the anesthesia or ventilation system of FIG. 1 according to one aspect of the present invention.

FIG. 2 is a perspective view of a dual filter assembly 20 according to one embodiment of the present invention. Dual filter assembly 20 comprises a first filter component 22 and a second filter component 24. First filter component 22 comprises a housing 26. Second filter component 24 comprises a housing 36. An inlet port 30 and outlet port 32 are positioned on opposing sides of housing 26 of first filter component 22. An inlet port 40 and outlet port 42 are positioned on opposing sides of housing 36 of second filter component 24. Additionally, housing 26 of first filter component 22 includes an annular member 56, while housing 36 of second filter component 26 includes an annular member 58.

In the illustrated embodiment, first filter component 22 is secured to second filter component 24 by means of a connector 60. Connector 60 comprises a strap having a length of at least 2 inches and no longer than 18 inches. In this manner, first filter component 22 and second filter component 24 are maintained in operable coupling to one another, minimizing the risk that a practitioner will fail to secure either first filter component 22 or second filter component 24 to an anesthesia/ventilation system 10 during an anesthesia removal procedure. In the illustrated embodiment, connector 60 is secured to the annular member 56 of first filter component 22 utilizing a securement member 62. Similarly, connector 60 is secured to annular member 58 of second filter component 24 utilizing a securement member 64. As will be appreciated by those skilled in the art, a variety of types and configurations of securement members can be utilized in connection with connector 60. According to one embodiment of the present invention, securement members 62 and 64 will provide a mechanical connection such as through the use of a rivet, snap fitting, screw, projection, or other known mechanical connectors. For example, according to one embodiment of the present invention, a mechanical connection is provided comprising a bonded strap placed through a loop that is formed, connected to or otherwise integrated into the housing of the filters. Alternatively, connector 60 can be connected to the housing 26 of first filter component 22 and the housing 36 of second filter component 24 using adhesives, magnetic securement or other known securement apparatus.

In the illustrated embodiment, one of inlet port 30 and outlet port 32 comprises a male connector, while the other of inlet port 30 and outlet port 32 comprises a female connector. Similarly, one of inlet port 40 and outlet port 42 comprise a male connector, while the other of inlet port 40 and outlet port 42 comprise a female connector. In this manner, inadvertent or accidental mistakes in the coupling of dual filter assembly 20 to an anesthesia/ventilation system 10 are minimized.

FIG. 3A is a close-up schematic view of an anesthesia/ventilation system 10 illustrating an inspiratory limb 16 and expiratory limb 18 in combination with dual filter assembly 20. In the illustrated embodiment, second filter component 24 is placed on expiratory limb 18. First filter component 22 is placed on inspiratory limb 16. In this manner, any gases or vapors that are flowing through expiratory limb 18 pass through second filter component 24. Any gases or vapors that are passing through inspiratory limb 16 pass through first filter component 22. As a result, any volatile anesthetics passing through expiratory limb 18 are adsorbed by second filter component 24. Any gases or vapors passing through inspiratory limb 16 are adsorbed by first filter component 22. In the illustrated embodiment, expiratory limb 18 comprises a first portion of expiratory limb 70 and a second portion expiratory limb 72. In one embodiment, first portion of expiratory limb 70 is tubing while second portion of expiratory limb 72 comprises a nipple, or male connector, of an anesthesia delivery device.

Second filter component 24 is positioned such that it is interposed between first portion of expiratory limb 70 and second portion of expiratory limb 72. First portion of expiratory limb 70 is positioned between a patient and second filter component 24. Second portion of expiratory limb 72 is positioned between the second filter component 24 and an anesthesia delivery device or other mechanical component which facilitates ventilation in connection with a breathing circuit.

In the illustrated embodiment, inspiratory limb 16 comprises a first portion of inspiratory limb 76 and a second portion of the inspiratory limb 78. First filter component 22 is interposed between first portion of inspiratory limb 76 and second portion of inspiratory limb 78. In one embodiment, second portion of inspiratory limb 78 is tubing while first portion of expiratory limb 76 comprises a nipple of an anesthesia delivery device. First portion of inspiratory limb 76 is positioned between first filter component 22 and an anesthesia delivery device or other mechanical component which facilitates ventilation in connection a breathing circuit. Second portion of inspiratory limb 78 is positioned between first filter component 22 and a patient.

In the illustrated embodiment, the pathway for fluid flow through expiratory limb 18 and inspiratory limb 16 is depicted. In the illustrated embodiment, an expired breath is shown after it has been expelled from the patient and enters first portion of expiratory limb 70. As the breath enters first portion of expiratory limb 70, the bulk of the volatile anesthesia which is being removed from the patient is removed in the form of an inhaled anesthetic is present in the gas positioned within expiratory limb 70. Depending on the particular aspects of the procedure being performed, the concentration of inhaled anesthetic within the first portion of expiratory limb 70 can vary anywhere from less than 100 parts per million up to at least 10,000 parts per million. For example, when the gas entering into first portion of expiratory limb 70 does not come from a patient, but is rather the result of circulation of gases through a ventilation system which has been adequately cleaned and scrubbed of volatile anesthetics, the amount of anesthesia entering into first portion of expiratory limb 70 can be as low as less than 100 parts per million. In contrast, in an inter-operative application in which an amount of inhaled anesthetics have been delivered to a patient and subsequently a malignant hyperthermia reaction is diagnosed, the amount of anesthetic entering first portion of expiratory limb 70 can be as high as up to 1 percent vapor or over 10,000 parts per million.

The positioning of second filter component 24 is such that second filter component 24 is positioned between first portion of expiratory limb 70 and second portion of expiratory limb 72. Because the exhaled vapor has not yet passed through second filter component 24, the amount of volatile anesthetic within the gas or vapor positioned within first portion of expiratory limb 70 is essentially the same concentration as the vapor when it was exhaled by the patient.

Figure 3B:
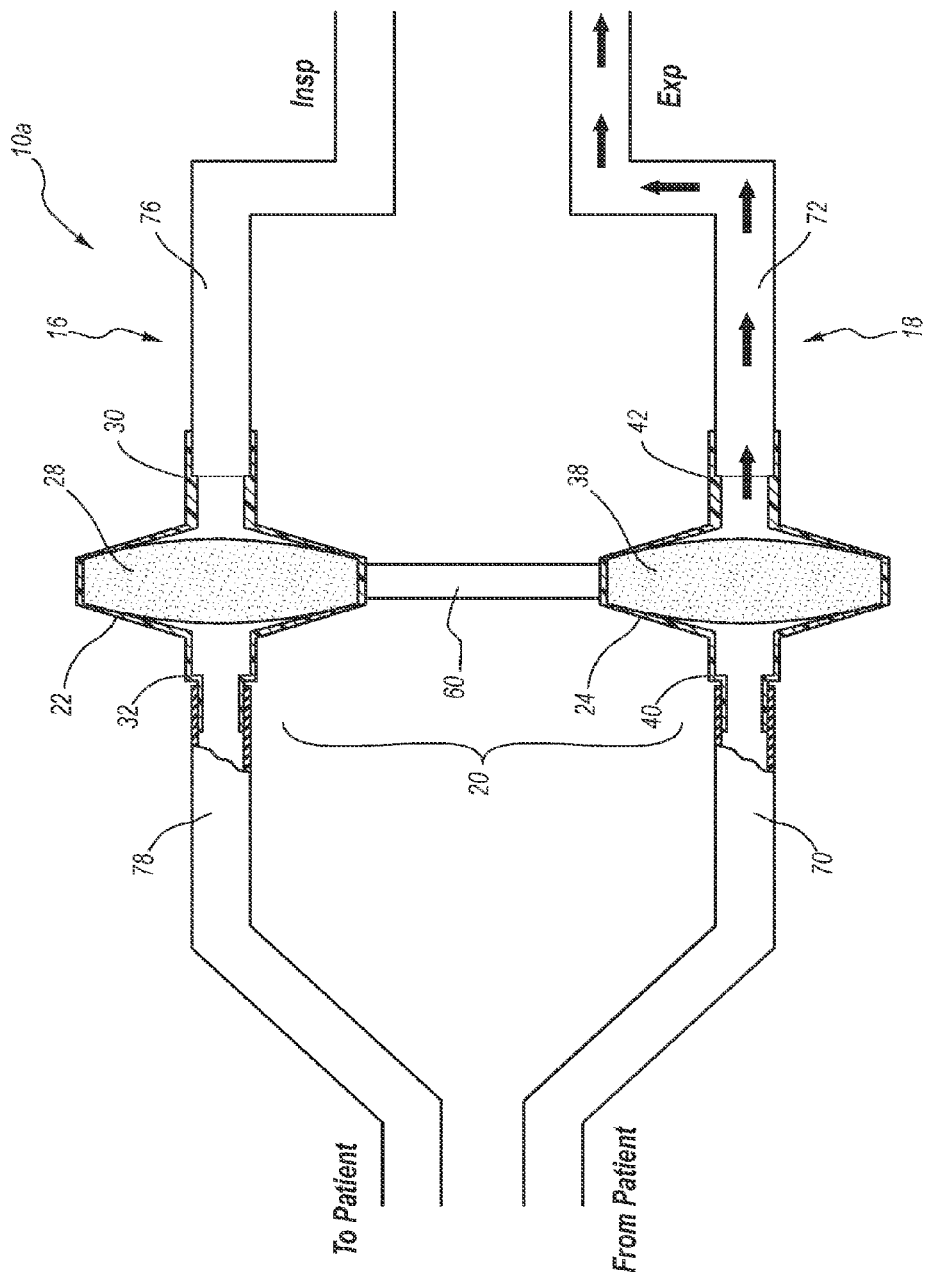

FIG. 3B is a perspective view of the anesthesia/ventilation system of FIG. 3A. In the illustrated embodiment, the exhaled gases have passed from first portion of expiratory limb 70 through second filter component 24 and have entered into the second portion of expiratory limb 72. As previously discussed, filter 38 associated with second filter component 24 removes volatile anesthetics from the gases or vapor passing from first portion of expiratory limb 70 to second portion of expiratory limb 72. As a result, the concentration of inhaled anesthetics or volatile anesthetics is substantially reduced. As a result, as the gases or vapors pass from second portion of expiratory limb 72 to the anesthesia machine, the concentration of such inhaled anesthetics have been substantially reduced.

As will be appreciated by those skilled in the art, during expiration, the volume of gases may remain fairly continuous from first portion of expiratory limb 70, through second filter component 24, into second portion of expiratory limb 72, and into the anesthesia machine. The illustration provided by FIGS. 3A and 3B depict schematically the mechanism by which the concentration of volatile anesthetics is reduced utilizing a second filter component 24 during the course of an expiration cycle in a ventilation system.

Figure 3C:
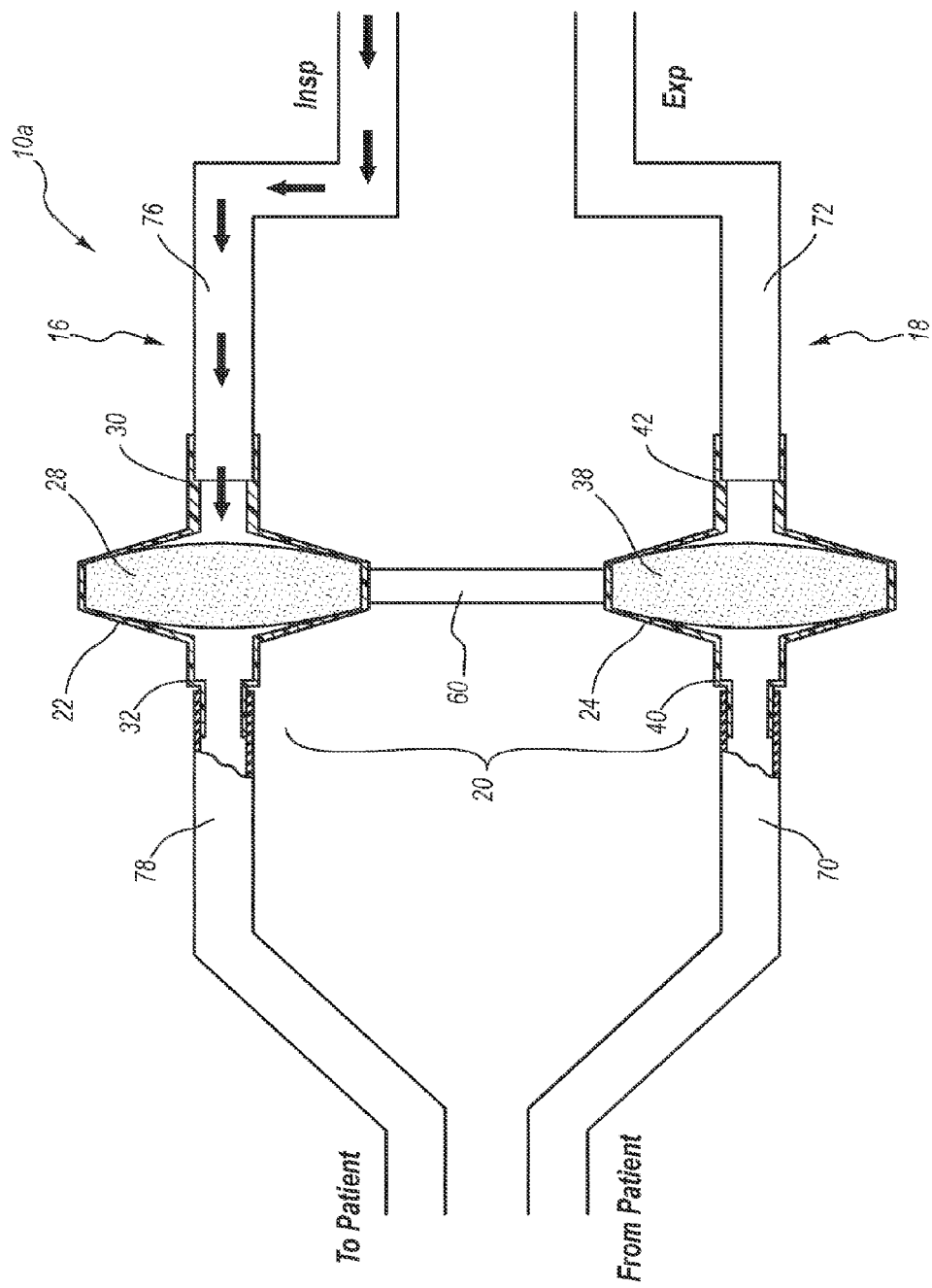

FIG. 3C depicts the passage of gases during an inspiratory cycle within a ventilation system. In the illustrated embodiment, gases are passing from an anesthetic delivery device to a first portion of inspiratory limb 76. At this stage in the inspiratory cycle, the gases have not yet passed through first filter component 22. As a result, the relative concentration of volatile anesthetics within first portion of the inspiratory limb 76 will be of a measurable concentration. In the event that a residual amount of such anesthetic vapors remains in the anesthesia machine, the concentration of such volatile anesthetics may be higher in first portion of inspiratory limb 76, that is currently depicted in FIG. 3C, than was present in second portion of expiratory limb 72, depicted in FIG. 3B. This is a result of the fact that such anesthetic residual vapor concentrations can remain in the synthetic materials within an anesthesia machine. Examples of different anesthesia machines can include a ventilator, monitoring system, oxygen delivery component, or other similar mechanisms. Even subsequent to a thorough flushing of the machine, and in some cases "scrubbing" of the anesthetic machine for several hours, such residual vapors can remain within the anesthetic machine. As a result, such concentrations of anesthetic vapor can be somewhat higher in first portion of inspiratory limb 76 than were present in second portion of expiratory limb 72.

Figure 3D:
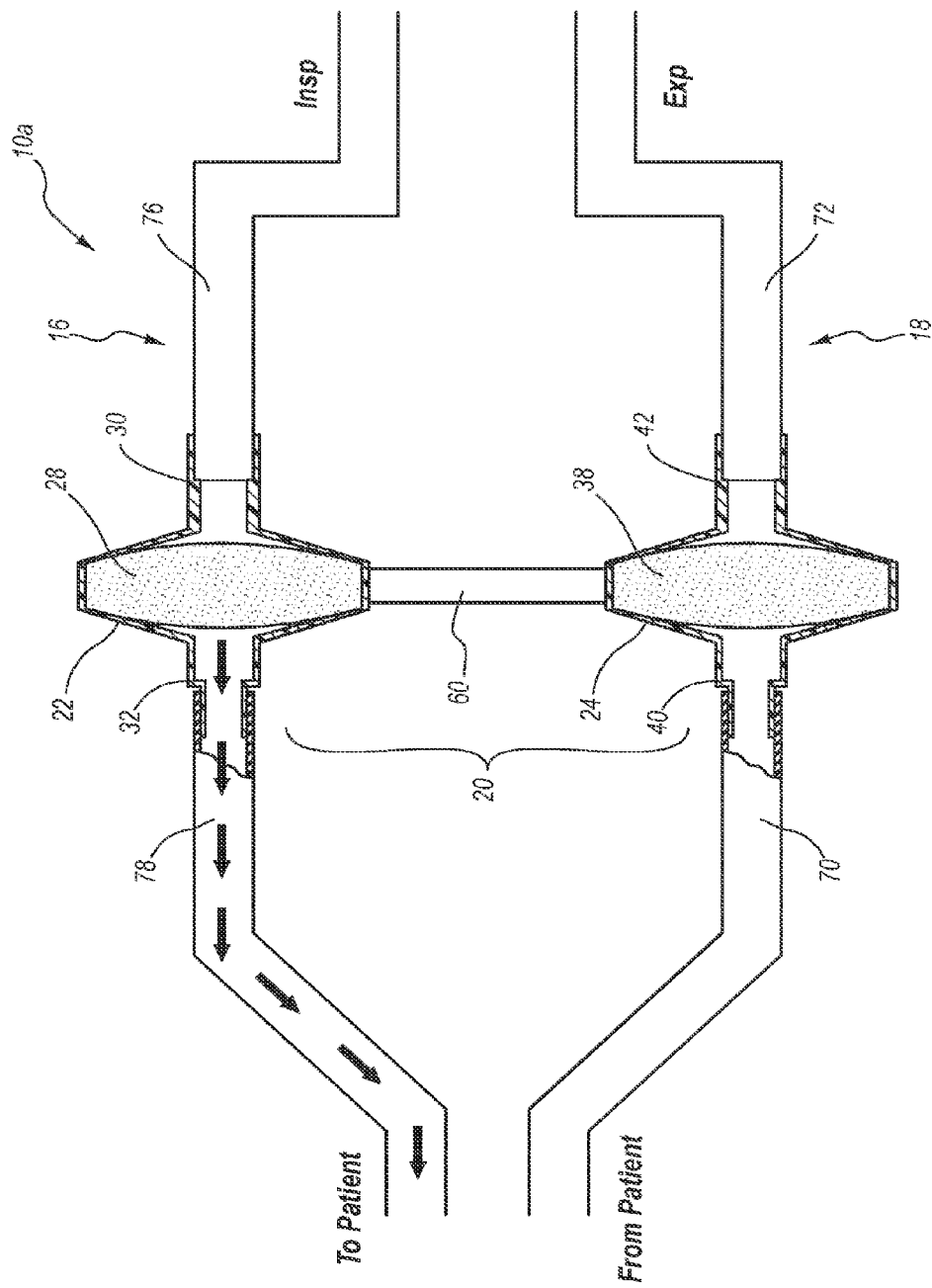

FIG. 3D depicts passage of the gases and vapors from first portion of inspiratory limb 76 through a first filter component 22 and into the second portion of inspiratory limb 78. Filter 28 is adapted to adsorb volatile anesthetics positioned within the gases that are passing from first portion of inspiratory limb 76 to second portion of inspiratory limb 78. As a result, the concentration of inhaled anesthetics in second portion of inspiratory limb 78 will be substantially less than the volume of gases within first portion of the inspiratory limb 76.

In the illustrated embodiment, the use of a dual filter assembly 20 having both a first filter component 22 and a second filter component 24 substantially reduces the volume of volatile anesthetics within an anesthesia/ventilation system 10a than can be provided with a single anesthesia filter. For example, in the event that the same volume of volatile anesthetics would need to be removed by a single filter as the volume of volatile anesthetics removed by the dual filter assembly of FIG. 3D, a thicker and more substantial filter would need to be provided. According to one embodiment of the present invention, anesthetic vapors are adsorbed by charcoal filter material when the molecules of anesthetic gas are trapped in an unoccupied and appropriately sized pore on the surface of a charcoal granule within the filter. According to an alternative embodiment of the present invention, the anesthetic vapors are removed by an anesthetic filter utilizing absorption.

In the event that a thicker charcoal bed is utilized in connection with a filter, the greater will be the likelihood that the molecule will be trapped in an available surface pore. If the filter bed does not provide sufficient volume, there is a possibility that molecules of anesthetic vapor may pass through the filter bed without being captured. The efficiency of the filter is proportional to the thickness of the bed of adsorbent material, or charcoal, within the filter. However, the use of a single thicker and more substantial filter can also increase the resistance to breathing experienced by the patient. As a result, while a single thick charcoal filter can increase the adsorptive properties of the filter, the filter can increase the difficulty of respiration as the patient breathes through the filter, or in other words, the portion of the system in which the filter is positioned.

The dual filter assembly provides improved removal of volatile anesthetic by providing a desired overall filter thickness and corresponding anesthetic removal volume while also minimizing the resistance to breathing imposed by a single thick filter. In other words, as vapor passes from first portion of expiratory limb 70 to second portion of expiratory limb 72, the amount of volatile anesthetic in the gas or vapor is substantially reduced by second filter component 24. As the gas flows from first portion of inspiratory limb 76 to second portion of inspiratory limb 78, the volume of volatile anesthetic within the gas or vapor is further reduced by first filter component 22. As a result, the concentration of inhaled anesthetic vapor can be reduced from as high as 1 percent vapor, or over 10,000 parts per million to less than 5 parts per million. As a result, dual filter assembly 20 provides an effective mechanism for not only removing volatile anesthetics from an anesthesia/ventilation system 10a, but also provides desired gaseous flow and lessened resistance to breathing while also ensuring that the gas reintroduced to the patient is substantially free of inhaled vapors that could create or further exacerbate a malignant hyperthermia condition.

Figure 4:
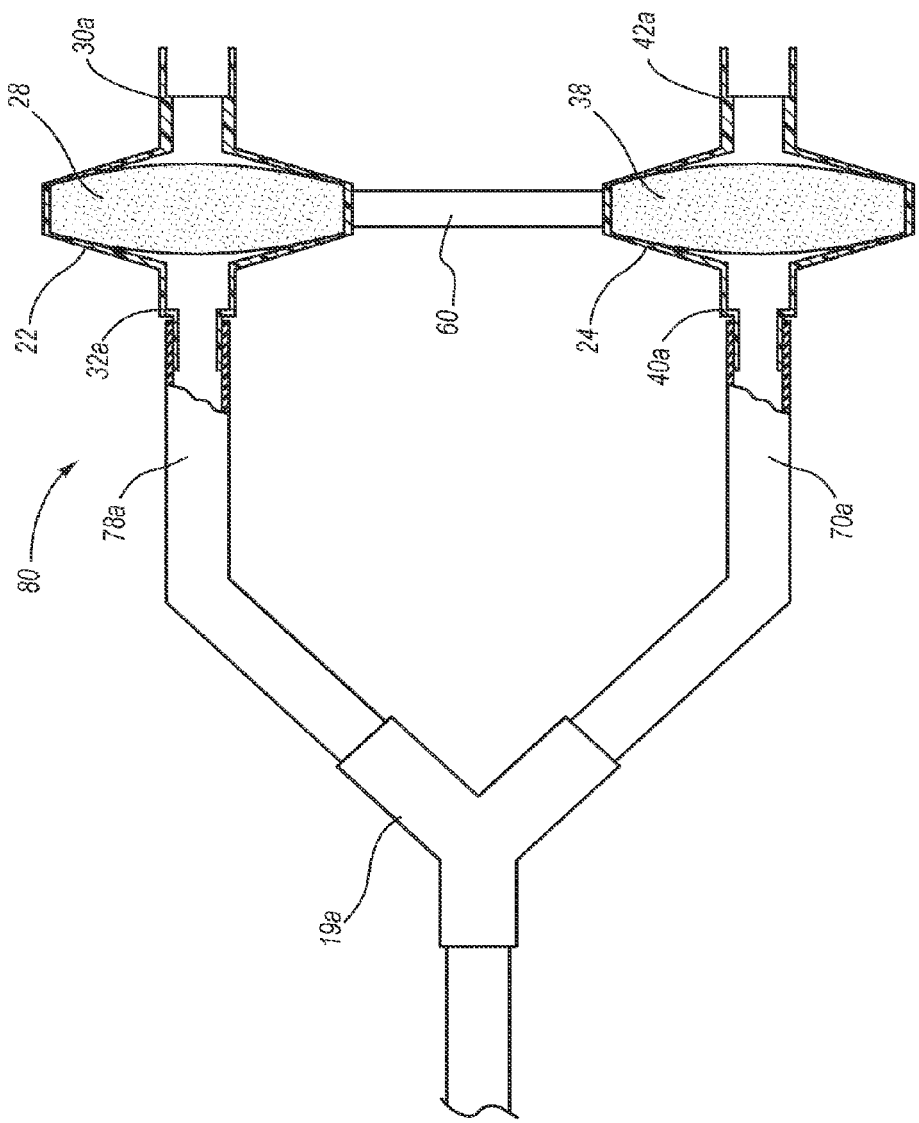
FIG. 4 is a schematic view of a breathing circuit having a dual filter assembly according to one embodiment of the present invention.

FIG. 4 is a schematic view of a breathing circuit 80 having a dual filter assembly according to one embodiment of the present invention. In the illustrated embodiment, breathing circuit 80 comprises a filter 22, a filter 24, an expiratory limb 70a, an inspiratory limb 78a and a branch component 19a. Filter 22 is secured to inspiratory limb 78a at the outlet port 32 of filter 22. Filter 24 is secured to expiratory limb 38 at the inlet port of 40 filter 24. Expiratory limb 70a is secured to inspiratory limb 78a at the distal end of each of expiratory limb 70a and inspiratory limb 78a utilizing branch component 19a. In the illustrated embodiment, the components of breathing circuit 80 are integrally coupled, bonded or otherwise fixedly secured to one another allowing a user to replace a contaminated breathing circuit with breathing circuit 80 in a simple and efficient manner.

Filter 22 includes an inlet port 30. Inlet port 30 comprises a female connector which can be secured to a male connector port of an anesthesia machine. Filter 24 includes an outlet port 42. Outlet port 42 comprises a female connector which can be secured to a male connector port of an anesthesia machine. A connector 60 is also depicted. Connector 60 secures filter 22 to filter 24. In this manner, the components of breathing circuit 80 are maintained in spatial and functional relationship to one another. In the illustrated embodiment, the components of breathing circuit 80 are integrally coupled, bonded or otherwise fixedly secured to one another, as a result, the user can simply and efficiently replace a contaminated breathing circuit with breathing circuit 80 in a simple and efficient manner. For example, the user can remove the contaminated breathing circuit, and simply secure inlet port 30 and outlet port 42 to the corresponding ports on the anesthesia machine. The branched component 19a can then be connected to the mask or other breathing apparatus connected to the patient.

As will be appreciated by those skilled in the art, a variety of types and configurations of breathing circuits can be utilized without departing from the scope and spirit of the present invention. For example, according to one embodiment of the present invention, one or both of the filters are removable from the breathing circuit. According to another embodiment of the present invention, the filters are configured to attach to tubing or extenders which are attached to the anesthesia machine. According to another embodiment of the present invention, the filters are contained within a single housing or are connected by a rigid connector member. According to yet another embodiment of the present invention, a connection is provided to the patient utilizing a mechanism other than a branched component. According to one embodiment of the present invention, the filters are not connected to one another utilizing a mechanical connector.

Figure 5:
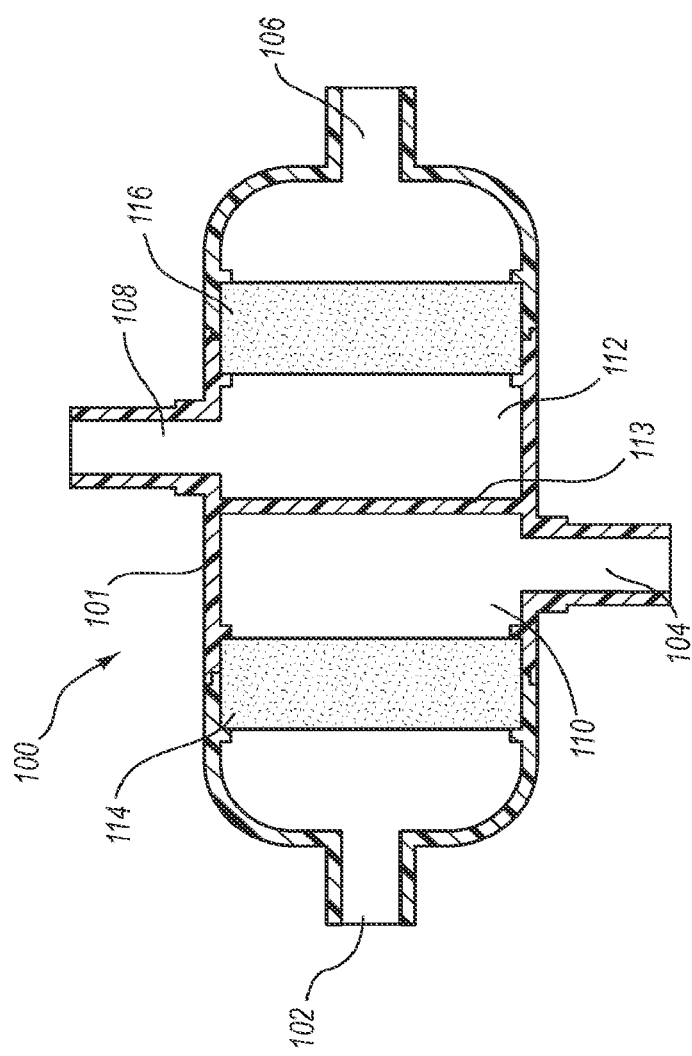
FIG. 5 is a cross-sectional view of a two-part filter apparatus for use in the removal of volatile anesthetics from an anesthesia or ventilation system according to one aspect of the present invention.

FIG. 5 is a perspective view of a two-part filter apparatus 100 according to one aspect of the present invention. In the illustrated embodiment, two-part filter apparatus 100 is one example of an apparatus for removing volatile anesthetics from an anesthesia or ventilation system. Two-part filter apparatus 100 comprises a housing 101, an expiratory inlet port 102, an expiratory outlet port 104, an inspiratory inlet port 106, and an inspiratory outlet port 108. Two-part filter apparatus 100 further comprises a first filter chamber 110, a second filter chamber 112, and a boundary septum 113. Boundary septum 113 divides the internal volume of two-part filter apparatus 100 into first filter chamber 110 and second filter chamber 112.

First filter chamber 110 is in fluid communication with expiratory inlet port 102 and expiratory outlet port 104. As a result, as expired gases pass into two-part filter apparatus 100 through expiratory inlet port 102, they pass into first filter chamber 110. Then as the gases pass from two-part filter apparatus 100, they are expelled from first filter chamber 110 and pass out of expiratory outlet port 104. A first filter 114 is positioned within filter chamber 110. First filter 114 comprises a carbon fiber or other known filter which is adapted to adsorb volatile anesthetics which may be present within gases passing through two-part filter apparatus 100. In the illustrated embodiment, as gas passes into expiratory inlet port 102 and out through expiratory outlet port 104, the gases pass through first filter 114 positioned within first filter chamber 110. In this manner, as expired gases leave the patient and pass through an expiratory limb, volatile anesthetics positioned within those gases will be removed by first filter 114 positioned in first filter chamber 110.

Second filter chamber 112 is associated with inspiratory inlet port 106 and inspiratory outlet port 108. In the illustrated embodiment, inspiratory inlet port 106 is adapted to receive a volume of gas which is passing from an anesthesia delivery system and into a patient. As a result, as the gases pass through an inspiratory limb and into inspiratory inlet port 106, the gases pass through a second filter 116 positioned within second filter chamber 112. Additionally, as the gases pass through second filter 116 and out of inspiratory outlet port 108, volatile anesthetics are removed from the gases passing through second filter chamber 112.

By providing a two-part filter apparatus 100, the benefits of having a first filter component and a second filter component are provided within a single self-contained apparatus. Boundary septum 113 maintains a fluid tight seal isolating first filter chamber 110 from second filter chamber 112. First filter 114 positioned within first filter chamber 110 can affectively remove volatile anesthetics from gases passing through an expiratory channel of an anesthesia/ventilation system. Inspiratory gases passing through an inspiratory channel with an anesthesia/ventilation system 10 can be removed by second filter 116 positioned within second filter chamber 112. In the illustrated embodiment, first filter chamber 110 comprises a defined fluid volume which is adapted to accommodate not only first filter 114, but also an additional amount of gaseous volume within the expiratory channel. Similarly, second filter chamber 112 defines a second fluid volume which contains not only second filter 116, but also a volume of fluid in addition to that which is positioned within second filter 116. In this manner, desired operation of two-part filter apparatus 100 can be maintained notwithstanding the particular geometries of the anesthesia/ventilation system.

In the illustrated embodiment, one or both of inlet port 102 and inlet port 106 comprise a female coupling component. In the embodiment, one or both of inspiratory outlet port 104 and inspiratory outlet port 108 comprise a male component. In this manner, a practitioner can quickly and easily ascertain the proper coupling of the two-part filter apparatus to an anesthesia/ventilation system 10.

According to another embodiment of the present invention, a failsafe mechanism is provided in connection with two-part filter apparatus 100. The failsafe mechanism is configured to allow practitioner to readily identify when an improper component of anesthesia/ventilation system 10 is coupled to one or more of expiratory inlet port 102, expiratory outlet port 104, inspiratory inlet port 106 or inspiratory outlet port 108. As a result, the practitioner can readily identify and correct the improper coupling before operation of the anesthesia/ventilation system is resumed. According to another embodiment of the present invention, the failsafe will not allow improper coupling or operation of the system to occur.

According to another embodiment of the present invention, two-part filter apparatus 100 is integrally coupled to the other components of the breathing circuit. For example, two-part filter apparatus 100 can be integrally coupled to primary expiratory limb 120 and primary inspiratory limb 128. In this manner, in the event that a patient experiences a malignant hyperthermic condition, the practitioner can readily remove the existing breathing circuit and replace the existing breathing circuit with a breathing circuit having an integrated two-part filter apparatus 100. In this manner, the practitioner can immediately provide filter gas having sufficiently low levels of volatile anesthetics to minimize or prevent further introduction of such volatile anesthetics to a patient. Additionally, the two-part filter apparatus 100 will be correctly positioned within the breathing circuit without requiring undue attention to the exact configuration of the two-part filter apparatus relative to the other components of the system.

As will be appreciated by those skilled in the art, a variety of the types and configurations of two-part filter apparatus can be utilized without departing from the scope and spirit of the present invention. For example, according to one embodiment of the present invention, the first filter chamber and second filter chamber are separated from one another utilizing something other than a boundary septum. According to another embodiment of the present invention, the geometries, configuration or other aspects of the two-part filter apparatus can be modified without departing from the scope and spirit of the present invention. For example, in one embodiment, the first filter chamber and second filter chamber are completely filled with a filter member. According to another embodiment of the present invention, one or both of the first filter chambers and second filter chambers are expandable to increase the fluid volume of the chamber. According to yet another embodiment of the present invention, the alignment of the first filter chamber relative to the second filter chamber facilitates practitioner recognition of correct coupling of the expiratory limb to the two-part filter apparatus, as well as the inspiratory limb to the two-part filter apparatus.

FIG. 6A is a perspective view of an anesthesia/ventilation system 10b according to one embodiment of the present invention. In the illustrated embodiment, anesthesia/ventilation system 10b primarily is illustrated to depict aspects of the inspiratory and the expiratory channels of the anesthesia/ventilation system 10b. In the illustrated embodiment, a primary expiratory limb 120, secondary expiratory limb 122, primary inspiratory limb 126, and secondary inspiratory limb 128 are provided. In the embodiment, primary expiratory limb 120 is secured to expiratory inlet port 102. Secondary expiratory limb 122 is secured to expiratory outlet port 104. Primary inspiratory limb 126 is secured to inspiratory inlet port 106. Secondary inspiratory limb 128 is secured to inspiratory outlet port 108. In this manner, during expiration, gases pass from primary expiratory limb 120 into first filter chamber 110 to secondary expiratory limb 122. From secondary expiratory limb 122, the gases pass to an anesthesia machine. In the illustrated embodiment, as gases pass from the anesthesia delivery system into primary inspiratory limb 126. From primary inspiratory limb 126, the gases pass into second filter chamber 112. As the gases flow through second filter chamber 112, they pass through second filter 116 and out of inspiratory outlet port. From the inspiratory outlet port 108, the gases pass into secondary inspiratory limb 128 and then can flow to the patient.

FIG. 6A depicts the passage of gas from a patient, such as during expiration into primary expiratory limb 120. As the gases pass into primary expiratory limb 120, they will tend to have a high concentration of volatile anesthetics. In the illustrated embodiment, the gases are beginning to pass not only into primary expiratory limb 120, but also into first filter chamber 110.

Figure 6B:
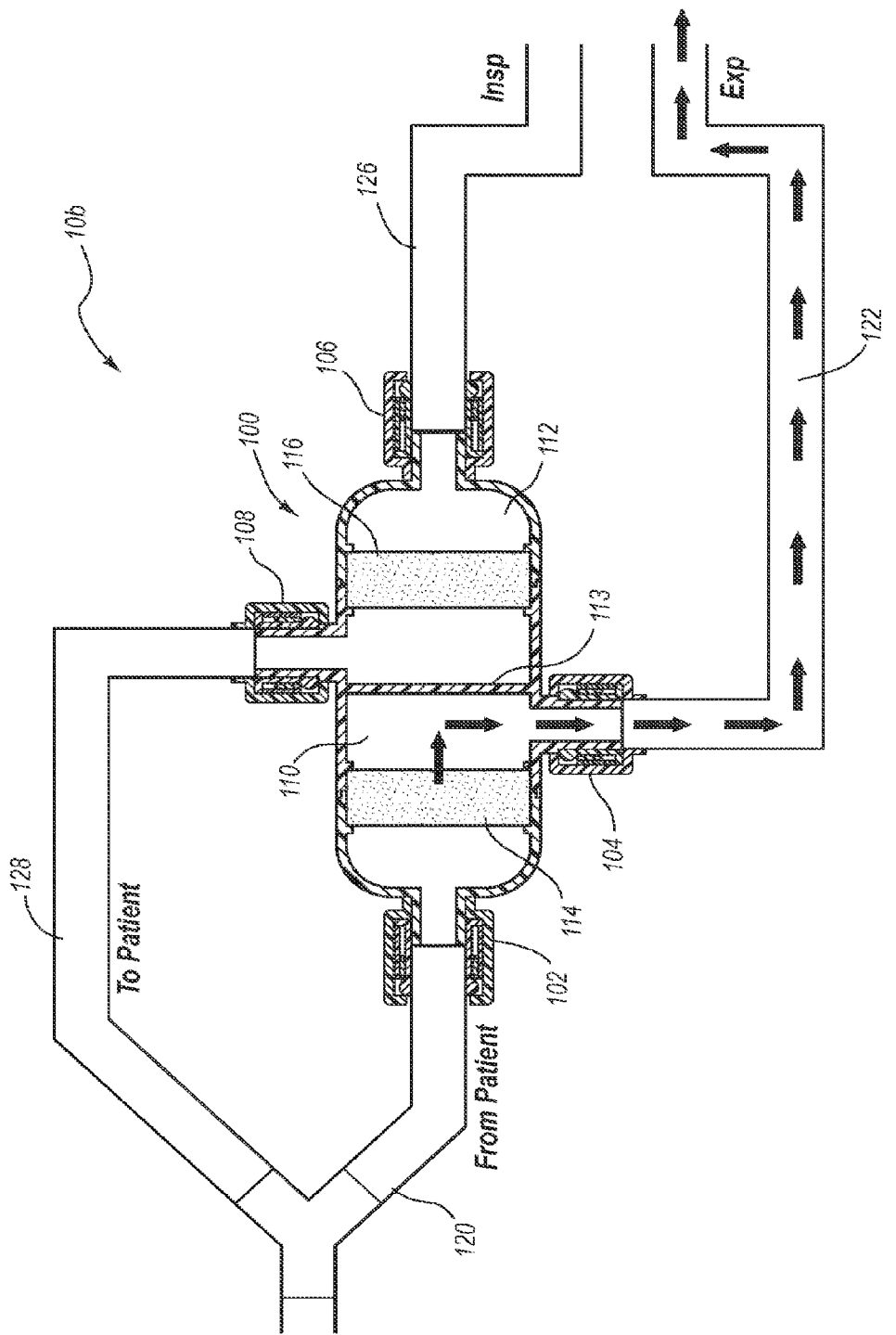

FIG. 6B is a perspective schematic view illustrating the passage of gases from first filter chamber into secondary expiratory limb 122. In the illustrated embodiment, as the gases pass from primary expiratory limb into secondary expiratory limb, they pass through first filter 114 positioned in first filter chamber 110. As the gases pass through first filter 114, volatile anesthetics are removed by first filter 114. As a result, the concentration of volatile anesthetics in the gases within secondary expiratory limb 122 will be substantially lower than the concentration of volatile anesthetics positioned within primary expiratory limb 120.

Figure 6C:
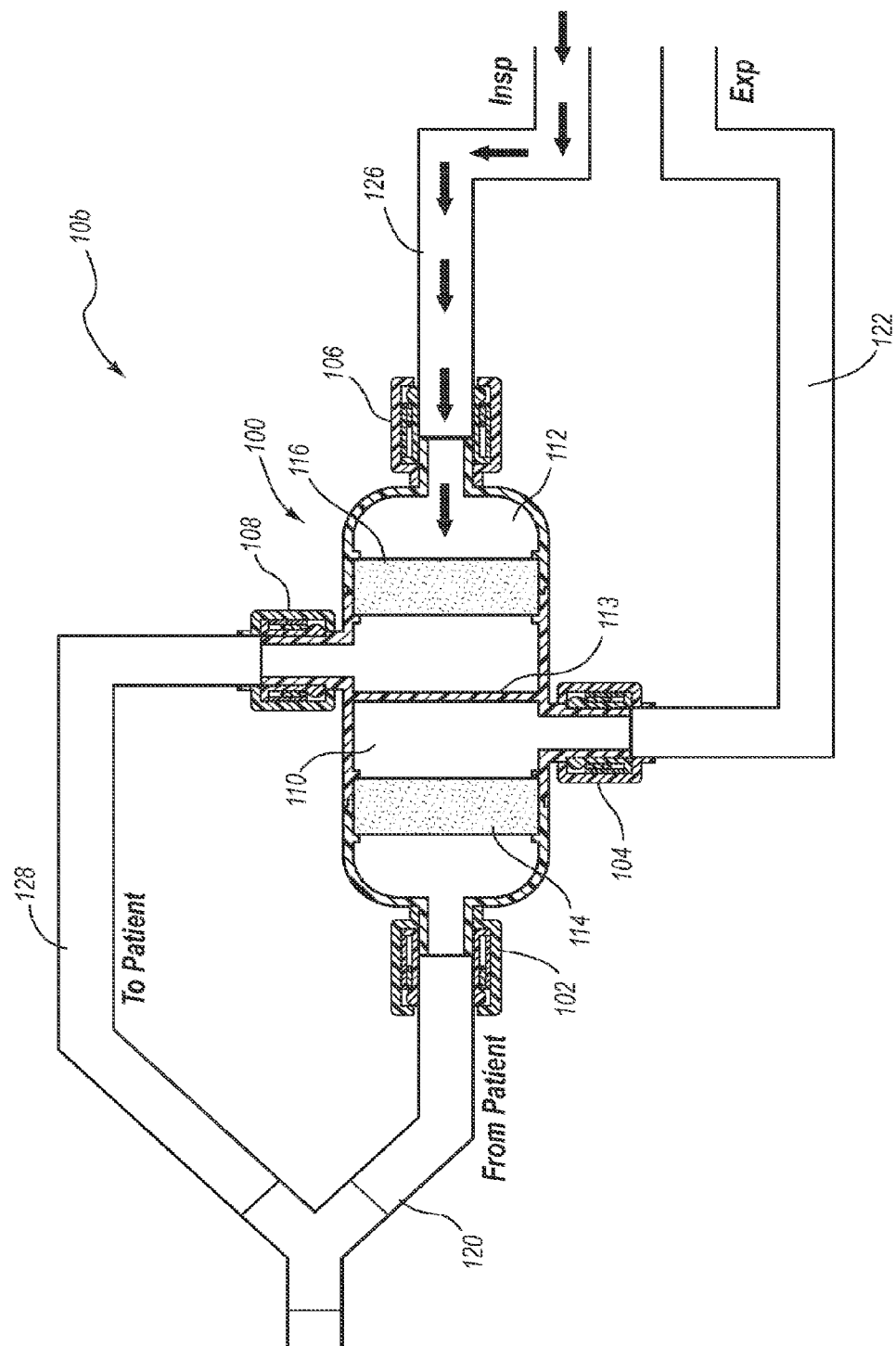

FIG. 6C illustrates the passage of gases through the inspiratory channels of anesthesia/ventilation system 10b. In the illustrated embodiment, gases are positioned in primary inspiratory limb 126. As the gases pass to primary inspiratory limb 126, they may have a slightly higher concentration of volatile anesthetics than the gases positioned in secondary expiratory limb 122. This is a result of the residual vapors that may reside within the anesthesia delivery system. As the gases begin to flow from primary inspiratory limb 126, they begin to pass into second filter chamber 112.

Figure 6D:
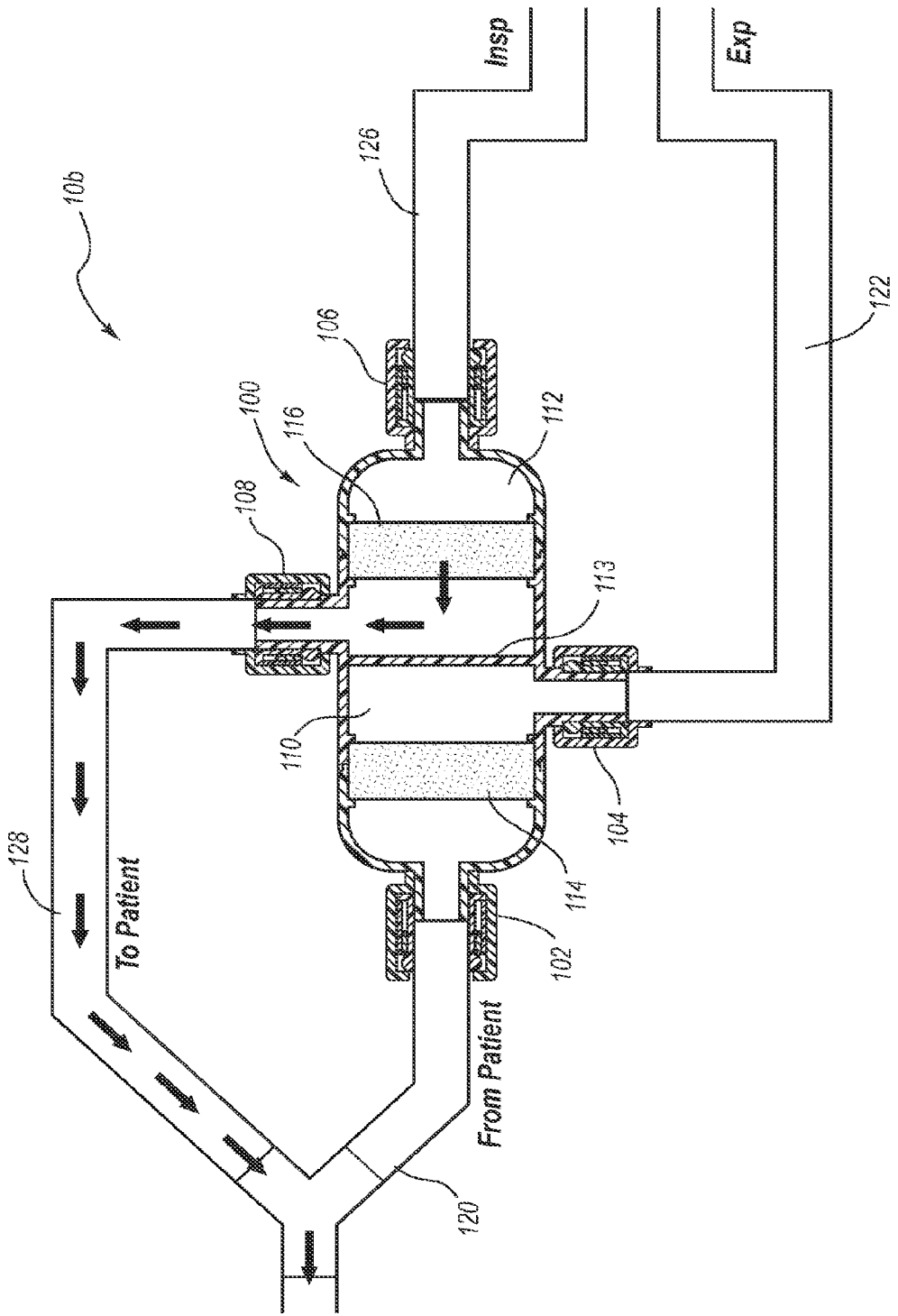

FIG. 6D illustrates passage of gases as they pass from second filter chamber 112 and into second inspiratory limb 128. As gases pass from primary inspiratory limb 126 to secondary inspiratory limb 128, the gases pass through second filter chamber 112 and thus through second filter 116. Second filter 116 comprises an anesthetic vapor removal filter. As a result, the gases positioned in secondary inspiratory limb 128 have a substantially reduced concentration of anesthetic when compared to the gases positioned within primary inspiratory limb 126.

As will be appreciated by those skilled in the art, the particular channels of flow and the particular connections of the two-part filter apparatus 100 with an anesthesia/ventilation system can vary without departing from the scope and spirit of the present invention. For example, according to one embodiment of the present invention, the two-part filter apparatus is adapted to connect to different portions of the anesthesia/ventilation system other than the inspiratory and expiratory limbs. According to another embodiment of the present invention, the inspiratory ports of the two-part filter apparatus are associated with tubes which connect to the inspiratory limbs while the expiratory ports do not have tubes allowing the practitioner to easily distinguish between inspiratory and expiratory channels of the two-part filter apparatus. According to another embodiment of the present invention, the angles and alignment of the first filter component of the two-part filter apparatus and the second filter component of the two-part filter apparatus are modified to allow easy distinguishing and detection of the different components.

Figure 7:
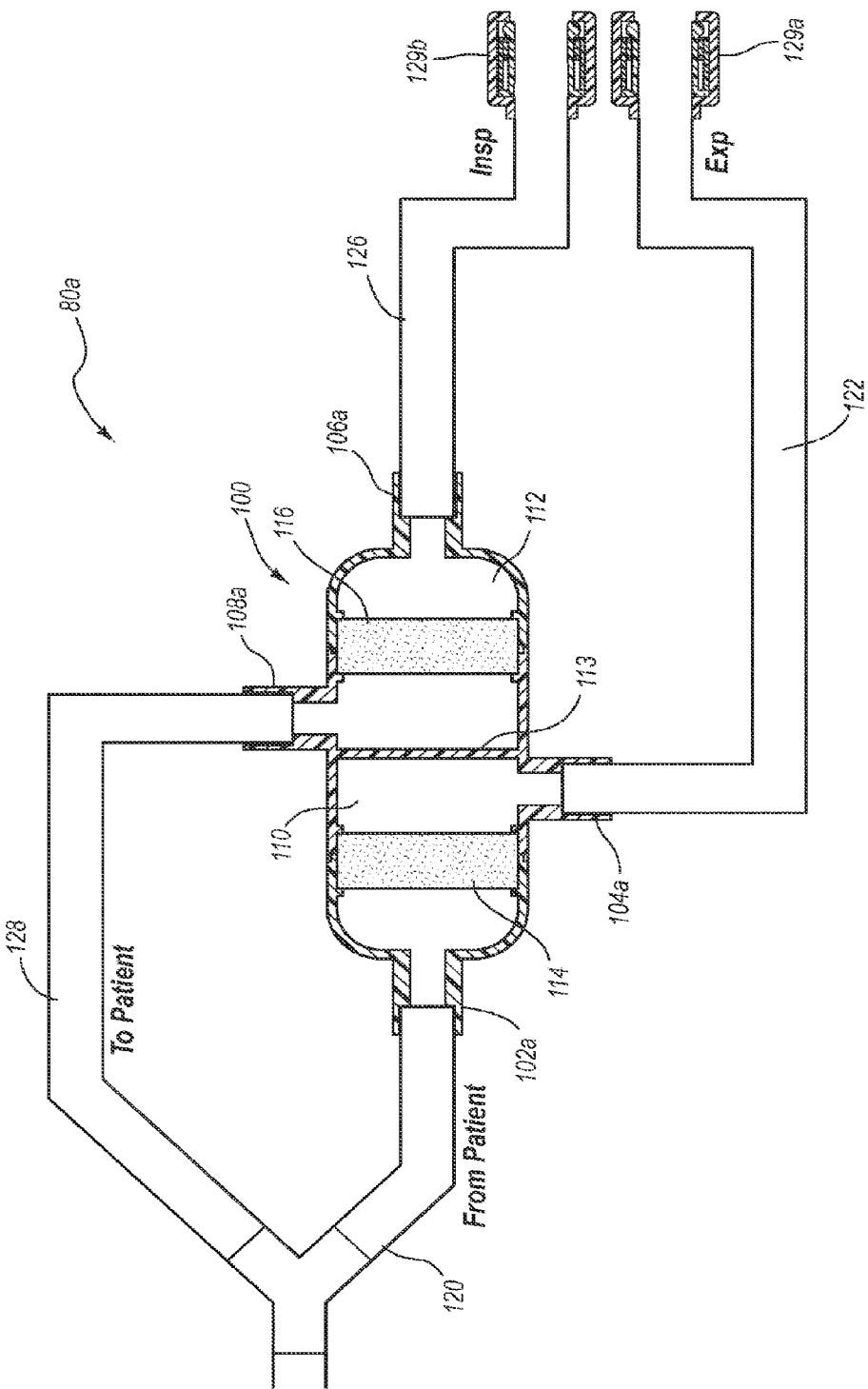
FIG. 7 is a schematic view of a breathing circuit having a two-part filter apparatus according to one embodiment of the present invention.

FIG. 7 is a schematic view of a breathing circuit 80a having a two-part filter apparatus according to one embodiment of the present invention. In the illustrated embodiment, two part filter apparatus 100 is integrally coupled to the inspiratory and expiratory limbs of the breathing circuit. In other words, expiratory inlet port 102a is coupled to primary expiratory limb 120. Expiratory outlet port 104a is integrally coupled to secondary expiratory limb 122. Inspiratory inlet port 106a is integrally coupled to primary inspiratory limb 126. Inspiratory outlet port 108a is integrally coupled to secondary inspiratory limb 128.

Female connectors 129a, b are provided in connection with breathing circuit 80a. Female connector 129a is connected to the proximal end of secondary expiratory limb 122. Female connector 129b is connected to the proximal end of primary inspiratory limb 126. The use of female connectors 129a, b allows breathing circuit to be quickly and simply connected to male connectors provided on an anesthesia machine. Additionally, the integral coupling of two part filter apparatus with the inspiratory and expiratory limbs provides an integrated breathing circuit 80a which can be quickly deployed and connected to an anesthesia machine in a preoperative or intra-operative setting.

As will be appreciated by those skilled in the art, a variety of types and configurations of breathing circuits can be provided without departing from the scope and spirit of the present invention. For example, according to one embodiment of the present invention, a connector is provided between the female connectors to space the connectors for ready securement to an anesthesia machine. According to another embodiment of the present invention, the filter includes female connectors such that the two part filter apparatus can be directly secured to the anesthesia machine. According to yet another embodiment of the present invention, one or more of the inlet and outlet ports of the two-part filter apparatus are removable from the associated tubing. According to yet another embodiment of the present invention, the two part filter apparatus has a housing in which the filter chambers are separated by the profile of the housing rather than by a boundary septum.

Figure 8:
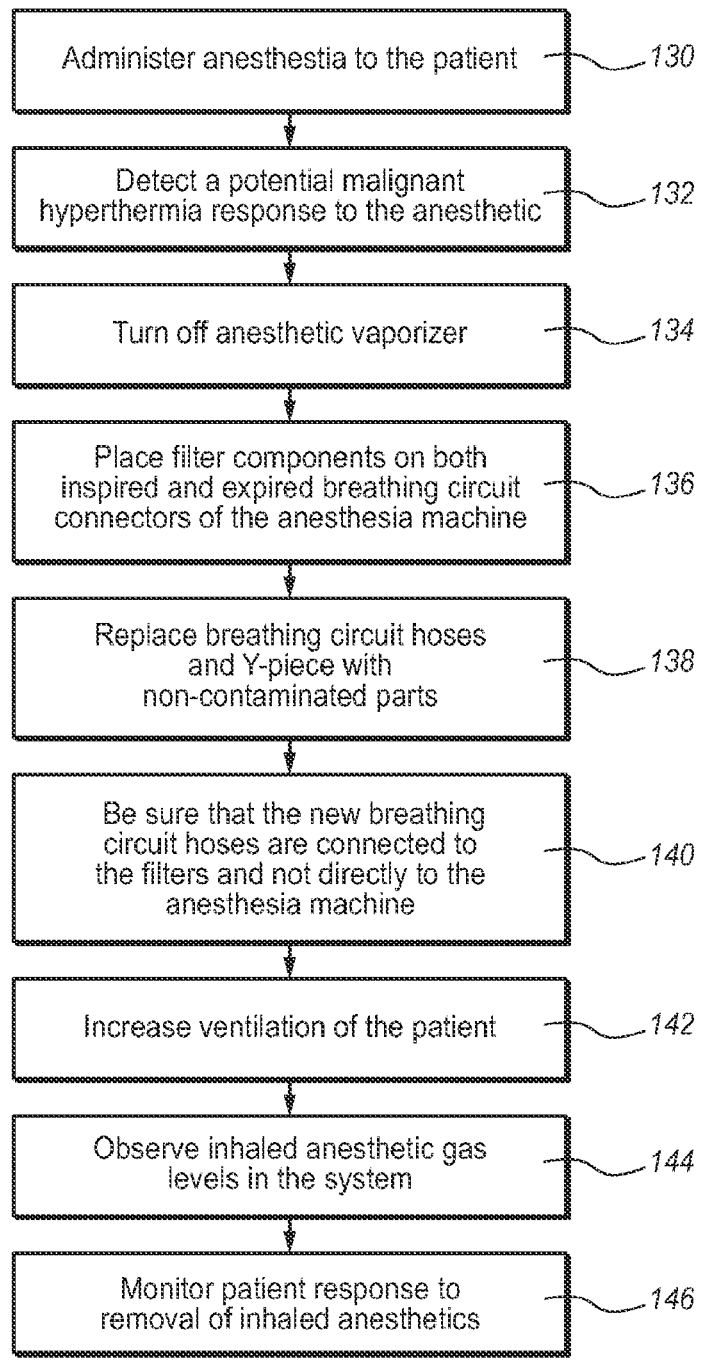
FIG. 8 is a flow chart illustrating a method of utilizing an anesthesia removal system or apparatus during the course of an anesthesia administration procedure.

FIG. 8 is a flow diagram illustrating a method of utilizing an apparatus for removing both the anesthetics from an anesthesia/ventilation system according to one embodiment of the present invention. In the illustrated embodiment, the method starts by administering anesthesia to a patient in a step 130. Once anesthesia has been administered to a patient in a step 130, a practitioner detects a potential hypothermic response to the anesthesia event in a step 132. The practitioner then turns off the anesthetic vaporizer in a step 134 to eliminate the introduction of new anesthetic vapors into the anesthesia/ventilation system. Once the anesthetic vaporizer has been turned off, the practitioner places a first filter component on an inspiratory limb of the anesthesia or ventilation system and a second filter component on the expiratory limb in a step 136. The practitioner then replaces the anesthesia breathing circuit with a non-contaminated breathing circuit in a step 138. Once the anesthesia breathing circuit has been replaced with a non-contaminated breathing circuit, then the practitioner can inspect the system to ensure that the hoses of the breathing circuit are properly connected to the filters, rather than being connected to the anesthesia machine in a step 140. The practitioner then increases patient ventilation utilizing the anesthesia/ventilation system in step 142. Increasing the ventilation can be effectuated by increasing the volume and rate of breaths given by the mechanical ventilator that is integrated into the anesthesia machine. Once the patient ventilation is increased, the practitioner can analyze and monitor levels of inhaled anesthetic within the system in a step 144. Subsequently, the practitioner can monitor patient response to the removal of the inhaled anesthetic and provide treatment to potential malignant hypothermic reactions in a step 146.

As will be appreciated by those skilled in the art, a method for reducing or eliminating volatile anesthetics from an anesthesia/ventilation system as depicted in FIG. 8 can be modified without departing from the scope and spirit of the present invention. For example, according to one embodiment of the present invention, placement of the two-part filter apparatus occurs in two steps subsequent to detection of a malignant hypothermic event with the first filter being secured to the inspiratory limb of the breathing circuit. According to another embodiment of the present invention, multiple steps occur simultaneously, such as turning off the anesthetic vapor, increasing fresh gas flow and flushing the circuit and finally placement of a filter apparatus.

Figure 9:
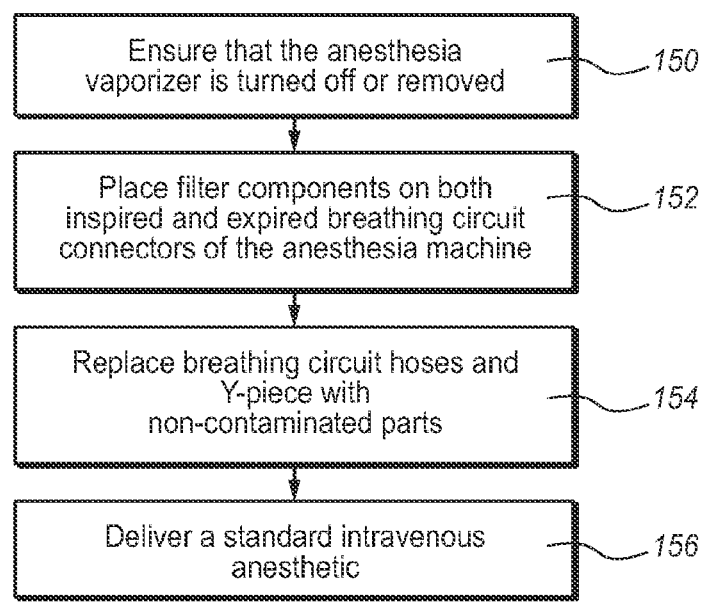
FIG. 9 is a flow chart illustrating a method for utilizing an anesthesia removal system and apparatus pre-operatively or post-operatively to minimize the effects of volatile anesthetic in an anesthesia or ventilation system according to one aspect of the present invention.

FIG. 9 is a flow diagram illustrating a method of removing volatile anesthetics from an anesthesia/ventilation system according to one embodiment of the present invention. In the illustrated embodiment, an anesthesia vaporizing component is operatively disconnected from an anesthesia system in a step 150. Once the anesthesia vaporizing component has been disconnected from the anesthesia system, an anesthesia filter, such as the two-part filter apparatus of FIG. 5, is connected to the anesthesia system with a first filter component being placed on the inspiratory limb and a second anesthesia filter is placed on the expiratory limb of the anesthesia machine in a step 152. Once the first filter and second filter have been connected to the anesthesia machine, the breathing circuit hoses are replaced with non-contaminated hoses in a step 154. The patient is then delivered a standard intravenous anesthetic in a step 154 and the anesthesia machine can be utilized for facilitating respiration of the malignant hyperthermia susceptible patient during the procedure in a step 156. In the illustrated embodiment, the method of FIG. 9 is adapted for use preoperatively or postoperatively to flush anesthetic from a ventilation of anesthetic system in order to minimize the potential that residual anesthetic could inadvertently be introduced into a patient who has a propensity toward malignant hyperthermia.

As will be appreciated by those skilled in the art, the use of an apparatus for removing volatile anesthetics from an anesthesia/ventilation system according to the present invention can be utilized with different methods and different order of steps without departing from the scope and spirit of the present invention. For example, in one embodiment, a two-part filter apparatus is connected to the ventilation system after scrubbing and flushing of the system to remove the system of volatile anesthetics, but before connection to a patient. In another embodiment, an apparatus such as a two-part filter is connected at the beginning of the scrubbing and flushing of the anesthesia system and before other aspects of the procedure are preformed. In another embodiment, no scrubbing or flushing of the system is necessary after the filters have been installed and the breathing circuit has been replaced. As a result, the machine can be utilized in a standard patient operation once the filters have been properly placed.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A filter apparatus for use with an anesthesia or ventilation system comprising:
   a housing having a first filter chamber connected to an inspiration limb of the ventilation system and a second filter chamber connected to an expiration limb of the ventilation system, wherein the first filter chamber comprises a first anesthetic gas adsorbing and removing filter configured to adsorb and remove anesthetic gas and provide inhaled gas to a patient that is substantially free of anesthetic gas, and the second filter chamber comprises a second anesthetic gas adsorbing and removing filter configured to adsorb and remove anesthetic gas and prevent release of such anesthetic gas to the patient, and wherein the first filter chamber and second filter chamber are not in fluid communication;
   a first inlet port and a first outlet port in fluid communication with the first filter chamber; and
   a second inlet port and second outlet port in fluid communication with the second filter chamber.

2. The filter apparatus for use with an anesthesia or ventilation system of claim 1, further comprising a separating member within the housing chamber separating the first filter chamber from the second filter chamber from fluid communication.

3. The filter apparatus for use with an anesthesia or ventilation system of claim 2, wherein the separating member is a boundary septum.

4. The filter apparatus for use with an anesthesia or ventilation system of claim 2, wherein the separating member is defined by the profile of the housing.

5. The filter apparatus for use with an anesthesia or ventilation system of claim 1, further comprising a tube connected to at least one of the first inlet port and the first outlet port wherein the tube distinguishes the first filter chamber from the second filter chamber.

6. The filter apparatus for use with an anesthesia or ventilation system of claim 1, wherein at least one of the first filter chamber and the second filter chamber are expandable to increase the fluid volume of the chamber.

7. A self-contained two-part filter apparatus comprising a housing having a first anesthetic removing filter component configured for attachment to the inspiratory limb of an anesthesia or ventilation system such that the first filter component is in fluid communication with an anesthetic passing through the inspiratory limb, wherein the first anesthetic removing filter component is configured to adsorb and remove anesthetic gas and provide inhaled gas to a patient that is substantially free of anesthetic qas, and a second anesthetic removing filter component configured for attachment to the expiratory limb of an anesthesia or ventilation system such that the second anesthetic removing filter component is in fluid communication with an anesthetic passing through the expiratory limb, and wherein the second anesthetic filter component is configured to adsorb and remove anesthetic gas and prevent release of such anesthetic qas to the patient, wherein the first anesthetic removing filter component and second anesthetic removing filter component are not in fluid communication and are each connected to a separate expiration and inhalation limb.

8. The self-contained two-part filter apparatus of claim 7, wherein the first anesthetic removing filter component comprises a first filter chamber and a first anesthetic removing filter disposed in the first filter chamber for removing volatile anesthetics passing through the first filter component.

9. The self-contained two-part filter apparatus of claim 8, wherein the second anesthetic removing filter component comprises a second filter chamber and a second anesthetic removing filter disposed in the second filter chamber for removing volatile anesthetics passing through the second filter component.

10. The self-contained two-part filter apparatus of claim 9, further comprising a separating member for maintaining a fluid tight seal isolating the first filter chamber from the second filter chamber.

11. The self-contained two-part filter apparatus of claim 7, wherein at least one of the first filter component and the second filter component comprises a filter chamber having a void therein, the void being sufficiently large to hold a filter and a fluid volume in addition to the filter.

12. A breathing circuit comprising the self-contained two-part filter apparatus of claim 7, the breathing circuit further comprising a first connector and a second connector for removably attaching the breathing circuit to an anesthesia or ventilation system.

13. The breathing circuit of claim 12, further comprising a separating member disposed between the first connector and the second connector.

14. A system for removing volatile anesthetics from an anesthesia system comprising:
an anesthesia machine;
a filter apparatus attachable to the anesthesia machine, the filter apparatus comprising a housing having a first filter chamber comprising a first anesthetic adsorbing and removing filter, wherein the first filter chamber is connected to an inspiratory limb of the ventilation system and the first anesthetic adsorbing and removing filter is configured to adsorb and remove anesthetic gas and provide inhaled gas to a patient that is substantially free of anesthetic gas, and a second filter chamber comprising a second anesthetic adsorbing and removing filter, wherein the second filter chamber is connected to an expiratory limb of the ventilation system and the second anesthetic adsorbing and removing filter is configured to adsorb and remove anesthetic gas and prevent release of such anesthetic gas to the patient, wherein the first filter chamber and second filter chamber are not in fluid communication and are each connected to a separate expiration and inhalation limb;
wherein the filter apparatus is attached to the anesthesia machine such that the first filter chamber is in fluid communication with the inspiratory limb of the anesthesia machine and the second filter component is in fluid communication with the expiratory limb of the anesthesia machine.

15. The system of claim 14, wherein the filter apparatus comprises a breathing circuit.

16. The system of claim 15, wherein the breathing circuit further comprising a first connector and a second connector for removably attaching the filter apparatus to the anesthesia machine.

17. The system of claim 14, wherein the filter apparatus further comprises a separating member for maintaining a fluid tight seal between the first filter chamber and the second filter chamber.

18. The system of claim 17, wherein the separating member is a boundary septum.

19. The system of claim 17, wherein the separating member is defined by the profile of the housing.

* * * * *